US007566764B2

(12) United States Patent
Gautier et al.

(10) Patent No.: US 7,566,764 B2
(45) Date of Patent: Jul. 28, 2009

(54) TRUNCATED BARD1 PROTEIN, AND ITS DIAGNOSTIC AND THERAPEUTIC USES

(75) Inventors: Fabien Gautier, Avrille (FR); Jean Harb, Nantes (FR); Khaled Meflah, Nantes (FR); Irmgard Irminger-Finger, Geneva (CH)

(73) Assignee: Ayanda Biosystems SA, Lausanne (CH)

( * ) Notice: Subject to any disclaimer, the term of this patent is extended or adjusted under 35 U.S.C. 154(b) by 1049 days.

(21) Appl. No.: 10/363,285

(22) PCT Filed: Sep. 3, 2001

(86) PCT No.: PCT/FR01/02731

§ 371 (c)(1),
(2), (4) Date: May 22, 2003

(87) PCT Pub. No.: WO02/18536

PCT Pub. Date: Mar. 7, 2002

(65) Prior Publication Data

US 2004/0234959 A1 Nov. 25, 2004

(30) Foreign Application Priority Data

Sep. 1, 2000 (FR) .................................. 00 11207

(51) Int. Cl.
*A61K 38/00* (2006.01)
*C07K 2/00* (2006.01)
*C07K 4/00* (2006.01)
*C07K 16/00* (2006.01)
*C07H 21/02* (2006.01)
*C12N 15/00* (2006.01)
*A01N 37/18* (2006.01)
*C07K 5/00* (2006.01)
*C07K 7/00* (2006.01)
*C07K 14/00* (2006.01)
*C07K 17/00* (2006.01)
*C07H 21/04* (2006.01)
*C12P 19/34* (2006.01)

(52) U.S. Cl. ...................... 530/300; 530/324; 536/23.1; 435/320.1; 435/91.1; 514/2

(58) Field of Classification Search ................. 530/300; 536/23.1; 435/325, 252.3; 424/130.1; 514/2
See application file for complete search history.

(56) References Cited

FOREIGN PATENT DOCUMENTS

WO    WO 98/12327    3/1998

OTHER PUBLICATIONS

Gura (Science, 1997, 278:1041-1042).*
Boon (Adv Can Res, 1992, 58:177-210).*
Verma et al (1997, Nature, vol. 389, p. 239-242).*
Marshall (1995) Science, vol. 269, p. 1050-1055).*
See Cheek (Nature, 2002, 420:116-118).*
Bowie et al (Science, 1990, 257:1306-1310).*
Burgess et al ( J of Cell Bio. 111:2129-2138, 1990).*
Lazar et al (Molecular and Cellular Biology, 1988; 8:1247-1252).*
Kleiman and Manley. Science 1999. vol. 285, pp. 1576-1579.*
Bodey, et al. Anticancer Research, 2000. vol. 20, pp. 2665-2676.*
Lee, et al. Journal of Immunology, 1999. vol. 163, pp. 6292-6300.*
Molecular expressions: the amino acid collection. http://micro.magnet.fsu.edu/aminoacids/index.html Apr. 22, 2008.*
To Hoa Thai et al: "Mutations in the BRCA1-associated Ring domain (BARD1) gene in primary breast, ovarian and uterine cancers"; Human Molecular Genetics, GB, Oxford University Press, Surrey, vol. 7, No. 2, 1998, pp. 195-202.
Gautier Fabien et al: "Identification of an apoptotic cleavage product of BARD1 as an autoantigen: A potential factor in the antitumoral response mediated by apoptotic bodies"; Cancer Research, vol. 60, No. 24, Dec. 15, 2000, pp. 6895-6900.
Wu L C et al: "Identification of a ring protein that can interact in vivo with THEBRCA1 gene product"; Nature Genetics, US, New York, NY, vol. 14, No. 4, Dec. 1, 1996, pp. 430-440.
Jian-Yu Wu, et al., "Aberrant expression of BARD1 in breast and ovarian cancers with poor prognosis," *Int. J. Cancer*: (2006) 118, 1215.
Irminger et al., 2007, Abstract 326, Posters:Gastrointestinal Pathology II/ Pathology-Research Practice 203 (2007):251-419.

* cited by examiner

*Primary Examiner*—David J. Blanchard
*Assistant Examiner*—Anne M. Gussow
(74) *Attorney, Agent, or Firm*—Saliwanchik, Lloyd & Saliwanchik

(57) ABSTRACT

The invention concerns a novel polypeptide derived from the cleavage of the BARD1 protein, a nucleic acid coding for said polypeptide, and their diagnostic and therapeutic uses, in particular for treating tumours.

20 Claims, 5 Drawing Sheets

```
                                    RING motif
                                                                        human
                                                                        Rat
                                                                        mouse MPDNRQPRNRQPRIRSGNEPRSAFAMEPDGRGAWAHSRAALDRLE.............
MP-----RRPPRVCSGNKPPPVPAMEPATDGLWAHSRAALARLE.............
MP-----RRPPRVCSGNQPAPVPAMEPATDGLWAHSRAAIARLE.............

IQDLKINRQLDSMIQLCSKLR  114
                        ILDLKINRQLDSMIQLYSKLQ  108
                        ILDLKINRQLDSMIQLSSKLQ  108

NLLHDNELSDLKEDKPRKSLFNDAGNKKNSIKMWFSPRSKKVRYVVSKASVQTQPA  168
NLLHDNKGSDSKDDTSRASLFGDAERKKNSVKMWFSPRSKKIRCVVNKVSVQTQPQ  162
NLLHDNK--DSKDNTSRASLEGDAERKKNSIKMWFSPRSKKVRYVVTKVSVQTQPQ  160

IKKDASAQQDS-YEFVSPSPPADVSERAKKASARSGKKQKKTLAEINQKWNLEAE   223
KAKDDKAQEASVFEFVSATPVVVSTRAKTASRTSAKKHPKKSVAKINREGNFRPE   218
KAKDDKAQEASMYEFVSATPVVAVPKSAKTASRTSAKKHPKKSVAKINREENLRPE  216

KEDGEFDSKEESKQKLVSFCSQPSVISSPQINGEIDLLASGSLTESECFGSLTEVS  279
TRDSRFDSKEKLKEEKVVSFSQTLVMENSRVNGEIDLLASGSVVESVFSGSFAEVS  274
TKDSRFDSKEELKEEKVVSCSQIPVMERPRVNGEIDLLASGSVVEPECSGSLTEVS  272

LPLAEQIESPDTKSRNEVVTPEKVCKNYLTSKKSLPLENNGKRGIHNRLSSPISKR  335
LPLAEHIVSPDTVSKSEEAPEKKVC------VEDRCPVGSDGNPKGCHRPPTSTSKK 325
LPLAEHIVSPDTVSKNEETPEKKVC------VKDLRSGGSNGNRKGCHRPTTSTSDS 323

FIG.1
```

```
o  |||  o|  ||  |  |oo|  o  o||oo  ool  |ooo
CRTSILSTSGDFVKQTVPSENIPLPECSSPPSCKRKVGGTGSRKNSNMSDEFISLS    391
CGSNVPSASGEIREPTLLAENVVLVDCSSLPSGRLQVDVTL-RRQSNASDDSLSLS   380
CGSNIPSTSRGIGEPALLAENVVLVDCSSLPSGQLQVDVTL-RKKSNASDDPLSLS   382
                                            ankyrin repeats ——▶
ooooo| o||o | oo |ooooo  |  ||            ooooooo oo|ooooo |oo o|ooo
PGTPPSTLSSSSYRQVMSSPSAMKLLPNMAV-KRNHR...   447
PGTPPSLLNNSTHRQMMSKPSTVKLSSGIPARKRNHR...   436
PGTPFFXLNNSTHRQMMSSPSTVKLSSGMPARKRNHR...   434 ooooo| ooooooooo  |ooooooooooooo oooooo|o|ooooooooo |o  o|ooooo
...                                        502
...                                        492
...                                        490 o|  ooo|  o  ooo| | | o|o|ooo|
...GLRPVDYTDDESMKSLLLPEKNESSSASHCS    558
...GERPVDYTDAENIRSLLLPEKTDSFSTSQCS    549
...GVRPVDYTDNENIRSLLLPEENESFSTSQCS    547
```

FIG. 1 continued

FIG.1 continued and end

TRUNCATED BARD1 PROTEIN, AND ITS DIAGNOSTIC AND THERAPEUTIC USES

CROSS REFERENCE TO PRIOR APPLICATION

This is a U.S. national phase application under 35 U.S.C. §371 of International Patent Application No. PCT/FR01/02731, filed Sep. 3, 2001, and claims the benefit of French Patent Application No. 00/11207, filed Sep. 1, 2000. The International Application was published in French on Mar. 7, 2002 as WO 02/018536 A2 under PCT Article 21(2).

The present invention relates to a novel polypeptide derived from cleavage of the BARD1 protein, and to its diagnostic and therapeutic uses.

The BARD1 protein is a 97 kD protein which interacts with the product of the BRCA1 tumor suppressor gene, via ring motifs present on BRCA1 and BARD1 (for "BRCA1Associated Ring Domain") (Wu et al., 1996). The gene encoding this protein has recently been cloned (WO98/12327).

The authors of the present invention have now identified a novel polypeptide which corresponds to a proteolytic fragment of BARD1, cleaved during the apoptotic process.

This truncated protein is very immunogenic and can be used, inter alia, in the treatment of cancers or in monitoring the effectiveness of the treatment with proapoptotic drugs of patients suffering from cancer.

A subject of the invention is therefore the isolated polypeptide which has a molecular weight of approximately 67 kD, as measured, for example, by electrophoresis under denaturing conditions (SDS-PAGE), and the sequence of which consists of the amino acid sequence of the BARD1 protein deleted of its N-terminal portion which comprises the RING domain.

More particularly, the polypeptide of the invention can be defined as consisting of approximately 505 to 525 amino acids from the C-terminal end of the human BARD1 protein (the known sequence of which is given in the annex SEQ ID No. 1). Even more particularly, the the polypeptide of the invention consists of 525 to 522 C-terminal amino acids of human BARD1 (SEQ ID NO:1).

The polypeptide of the invention can, for example, be purified from the apoptotic bodies derived from colon or mammary carcinoma cell lines.

More particularly, the polypeptide of the invention can be obtained using the method consisting in:
- culturing cells to confluency, for example cells belonging to a cell line such as PROb, SW48 or MCF7;
- inducing apoptosis of these cells by treating them with a culture medium containing 5 mM sodium butyrate (NaB), at 37° C. for 24 hours;
- adding isolated recombinant BARD1 protein;
- incubating for a sufficient amount of time, for example 60 minutes at 37° C., so as to observe cleavage of the BARD1 protein to a 67 kDa form.

The polypeptide of the invention is recognized by an antibody directed against a polypeptide corresponding to amino acids 255 to 265 of BARD1 (SEQ ID NO:1).

The authors of the invention have, moreover, shown that hydrolysis of BARD1 occurs at an early stage of apoptosis and in a cell cycle-dependent manner. This hydrolysis is inhibited by EGTA and the calpain inhibitor I, N-acetyl-leu-leu-norleucinal (ALLnL), but not by several caspase inhibitors, which suggests hydrolysis by calcium-dependent cysteine proteases, calpains.

Any protein consisting of a sequence homologous to said sequence of 505 to 525 amino acids of SEQ ID NO:1 is also included in the definition of the 67 kD polypeptide.

The expression "homologous amino acid sequence" is intended to mean a sequence at least 70%, preferably 80%, more preferably 90%, similar to said sequence of 505 to 525 amino acids of SEQ ID NO:1.

The term "similar" refers to the complete resemblance or identity between the amino acids compared, but also to the incomplete resemblance, which is referred to as similarity. This search for similarity in a polypeptide sequence takes into account the conservative substitutions, which are substitutions of amino acids of the same class, such as substitutions of amino acids with uncharged side chains (such as asparagine, glutamine, serine, threonine, or tyrosine), of amino acids with base side chains (such as lysine, arginine or histidine), of amino acids with acidic side chains (such as aspartic acid or glutamic acid), of amino acids with apolar side chains (such as glycine, alanine, valine, leucine, isoleucine, proline, phenylalanine, methionine, tryptophan or cysteine).

More generally, the expression "homologous amino acid sequence" is therefore intended to mean any amino acid sequence which differs from said sequence by substitution, deletion and/or insertion of an amino acid or of a small number of amino acids, in particular by substitution of natural amino acids with unnatural amino acids or pseudo amino acids, at positions such that these modifications do not significantly affect the biological properties mentioned above.

Homology is generally determined using sequence analysis software (for example, Sequence Analysis Software Package of the Genetics Computer Group, University of Wisconsin Biotechnology Center, 1710 University Avenue, Madison, Wis. 53705). Similar amino acid sequences are aligned so as to obtain the maximum degree of homology (i.e. identity or similarity, as defined above). For this purpose, it may be necessary to artificially introduce gaps into the sequence. Once the optimal alignment has been carried out, the degree of homology is established by recording all the positions for which the amino acids of the two compared sequences are identical, with respect to the total number of positions.

The polypeptide of the present invention can be synthesized by all the methods well known to those skilled in the art. The polypeptide of the invention can, for example, be synthesized by the techniques of synthetic chemistry, such as synthesis of the Merrifield type, which is advantageous for reasons of purity, of antigenic specificity and of absence of undesired side products, and for its use of production.

The protein produced can then be recovered and purified.

The methods of purification used are known to those skilled in the art. The recombinant polypeptide obtained can be purified from cell lysates and extracts and/or from the culture medium supernatant, by methods used individually or in combination, such as fractionation, chromatography methods, immunoaffinity techniques using specific mono- or polyclonal antibodies, etc.

The polypeptide of the invention may, in particular, be purified from apoptotic bodies originating from tumor cells, by affinity chromatography on a column of antibodies specific for the C-terminal end of the BARD1 protein.

The nucleic acid sequence encoding the truncated BARD1 protein can be inserted into an expression vector, in which it is functionally linked to elements for regulating its expression, such as in particular promoters, activators and/or terminators of transcription.

A recombinant protein can then also be produced using a method in which a vector containing a nucleic acid as defined above is transferred into a host cell, which is cultured under conditions allowing the expression of the corresponding polypeptide.

The signals controlling the expression of nucleotide sequences (promoters, activators, termination sequences, etc.) are selected as a function of the cellular host used. To this effect, the nucleotide sequences according to the invention can be inserted into vectors which replicate autonomously within the selected host, or vectors which integrate in the selected host. Such vectors will be prepared according to the methods commonly used by those skilled in the art, and the clones resulting therefrom can be introduced into a suitable host by standard methods, such as, for example, electroporation or calcium phosphate precipitation.

The cloning and/or expression vectors as described above, comprising a defined nucleotide sequence according to the invention, are also part of the present invention.

The invention is also directed toward the host cells transfected, transiently or stably, with these expression vectors. These cells can be obtained by introducing, into prokaryotic or eukaryotic host cells, a nucleotide sequence inserted into a vector as defined above, and then culturing said cells under conditions allowing the replication and/or expression of the transfected nucleotide sequence.

The properties of the truncated BARD1 protein according to the invention, or of the nucleic acid encoding this protein, as a tumor repressor can be taken advantage of in the treatment of tumors. This may involve any type of tumor, but more particularly breast cancers, ovarian cancers, lung cancers or cancers of the digestive tract, such as colon carcinomas.

A subject of the invention is therefore also a pharmaceutical composition comprising a polypeptide as defined above, or a nucleic acid encoding said polypeptide, in combination with a pharmaceutically acceptable vehicle.

The methods of administration, the doses and the pharmaceutical forms of the pharmaceutical compositions according to the invention, containing at least one polypeptide, can be determined in the usual manner by those skilled in the art, in particular according to the criteria generally taken into account in establishing a therapeutic treatment suitable for a patient, such as, for example, the age or bodyweight of the patient, the seriousness of his or her general condition, the tolerance to the treatment, and the side effects noted, etc.

In general, a therapeutically or prophylactically effective amount ranging from approximately 0.1 µg to approximately 1 mg can be administered to human adults.

The subject of the invention is also a pharmaceutical composition comprising a nucleic acid as defined above, encoding the truncated BARD1 protein, and a pharmaceutically acceptable vehicle, said composition being intended to be used in gene therapy. The nucleic acid, preferably inserted into a vector, generally a viral vector (such as adenoviruses and retroviruses), can be administered in naked form, free of any vehicle promoting transfer to the target cell, such as anionic liposomes, cationic lipids, microparticles, for example gold microparticles, precipitating agents, for example calcium phosphate, or any other agent facilitating transfection. In this case, the polynucleotide can be simply diluted in a physiologically acceptable solution, such as a sterile solution or a sterile buffer solution, in the presence or absence of a vehicle.

Alternatively, a nucleic acid of the invention can be combined with agents which facilitate transfection. It may, inter alia, be (i) combined with a chemical agent which modifies cellular permeability, such as bupivacaine; (ii) encapsulated in liposomes, optionally in the presence of additional substances facilitating transfection; or (iii) combined with cationic lipids or microparticles of silica, of gold or of tungsten.

When the nucleic acid constructs of the invention coat microparticles, these microparticles can be injected intradermally or intraepidermally via the "gene gun" technique (WO 94/24263).

The amount to be used as a medicinal product depends in particular on the nucleic acid construct itself, on the individual to whom this nucleic acid is administered, on the method of administration and the type of formulation, and on the pathological condition. In general, a therapeutically or prophylactically effective amount ranging from approximately 0.1 µg to approximately 1 mg, preferably from approximately 1 µg to approximately 800 µg, and preferentially from approximately 25 µg to approximately 250 µg, can be administered to human adults.

The nucleic acid constructs of the invention can be administered via any conventional route of administration, such as in particular parenterally. The choice of the route of administration depends in particular on the formulation selected. An administration targeted to the site of the tumors targeted may be particularly advantageous.

Finally, a subject of the invention is therefore a method of therapeutic treatment, in which an effective amount of a truncated BARD1 protein as defined above, or a nucleic acid encoding this protein is administered to a patient requiring such a treatment, in the context of a gene therapy.

The intended patient is generally a human, but the application may also be extended to any mammal where appropriate.

The appearance of the truncated form of BARD1, which appears during apoptic processes, makes it possible, moreover, to follow, in vitro, the effectiveness of an anticancer treatment in a patient treated with pro-apoptopic drugs. For this, it is possible to use a method of in vitro detection of the 67 kD polypeptide of the invention in a biological sample, such as a sample of tumor tissues.

According to a variant, a method of in vitro detection of antibodies produced against the immunogenic 67 kD polypeptide, in a biological sample, such as a blood or urine sample from patients, can be used.

These methods can make use of the usual techniques of immunodetection, such as Western Blotting or immunohistochemistry for example, using an anti-BARD1 or anti-truncated BAR1 antibody, when it involves detecting the 67 kD polypeptide, or using said polypeptide or an epitope fragment thereof, when it involves detecting the antibodies.

More generally, the invention is also directed toward a method of in vitro detection of truncated BARD1 polypeptide or of anti-truncated BARD1 antibodies in a biological sample in which said biological sample is brought into contact with, respectively, an anti-truncated BARD1 antibody or a truncated BARD1 protein, or an epitope fragment, and the formation of immunocomplexes is observed, revealing the presence of truncated BARD1 protein or of anti-truncated BARD1 antibodies, respectively, in the biological sample.

The antibodies which are specifically directed against the truncated BARD1 protein are also part of the invention.

They may be poly- or monoclonal antibodies or fragments thereof, chimeric, in particular humanized or immunoconjugated, antibodies, or else labeled antibodies.

The polyclonal antibodies can be obtained from the serum of an animal immunized against a polypeptide according to the usual procedures.

According to one embodiment of the invention, a suitable peptide fragment of the BARD1 protein, which can be coupled via a reactor residue to a protein or another peptide, can be used as antigen. Rabbits are immunized with the equivalent of 1 mg of the peptide antigen according to the procedure described by Benoit et al. (1982). At four-week intervals, the animals are treated with injections of 200 µg of antigen, and bled 10 to 14 days later. After the third injection, the antiserum is examined in order to determine its ability to bind to the antigenic peptide, radiolabeled with iodine, prepared by the chloramine-T method, and is then purified by chromatography on a carboxymethylcellulose (CMC) ion exchange column. The antibody molecules are then collected from the mammals and isolated to the desired concentration by methods well known to those skilled in the art, for example using DEAE Sephadex to obtain the IgG fraction.

In order to improve the specificity of the polyclonal serum, the antibodies can be purified by immunoaffinity chromatography using immunizing polypeptides in solid phase. The antibody is brought into contact with the immunizing polypeptide in solid phase for a sufficient amount of time so as to immunoreact the polypeptide with the antibody molecule in order to form an immunocomplex in solid phase.

The monoclonal antibodies can be obtained according to the conventional method of hybridoma culture described by Köhler and Milstein (1975).

The following examples and figures illustrate the invention without limiting the scope thereof.

LEGENDS OF THE FIGURES

FIG. 1 shows an amino acid sequence alignment for the human (SEQ ID NO:1), rat (SEQ ID NO:6) and mouse (SEQ ID NO:5) BARD1 proteins. The sequences corresponding to the RING motif, to the three ankyrin repeats and to the two BRCT domains in tandem are marked. The conserved Q564H mutation of the BARD1 human protein is also indicated. The sequences are aligned by introducing gaps so as to attain the maximum identity of the amino acid sequences. The values for the amino acids identity are then calculated by considering each space as a single dissimilarity (Table 1). The rat BARD1 cDNA sequence is available on EMBL under the accession number AF182946 (SEQ ID NO:10), that of mouse under the number AF057157 (SEQ ID NO:8) and that of humans under the Genbank number U76638 (SEQ ID NO:7).

Figure 3:
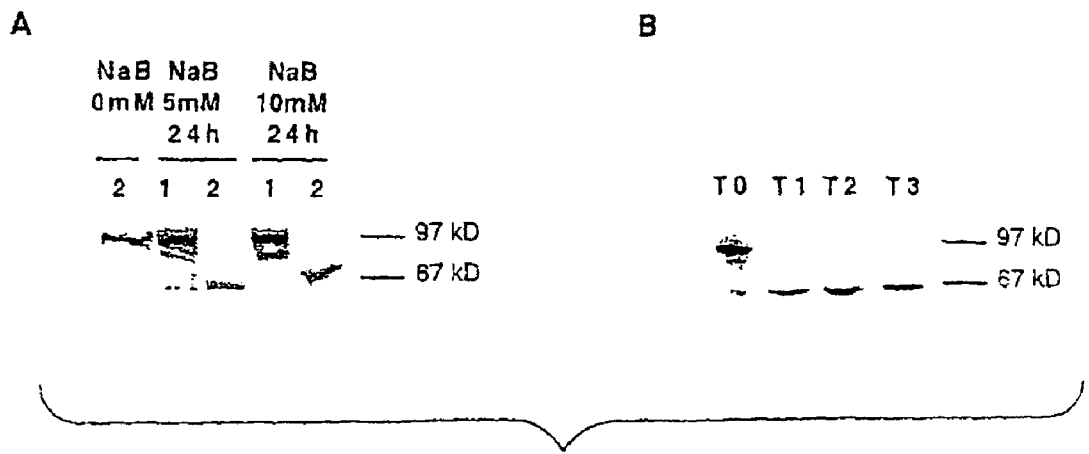

FIG. 3A represents an analysis of the products of in vitro hydrolysis of the human BARD1 protein (SEQ ID NO:1) by SW48 cell lysates treated at confluency with 5 mM of sodium butyrate for 24 hours. The apoptotic bodies recovered from the supernatant (1) or the adherent cells (2) were solubilized in a DIV buffer and added to a human BARD1 protein labeled with $^{35}$S-methionine. After incubation for 4 hours at 37° C., the hydrolysis products were separated by SDS-PAGE and autoradiographed using phosphorimager.

FIG. 3B represents the same type of analysis, the adherent cells being solubilized in DIV buffer and incubated with a human BARD1 protein labeled with $^{35}$S-methionine for 0 to 3 hours respectively (T0 to T3).

Figure 4:
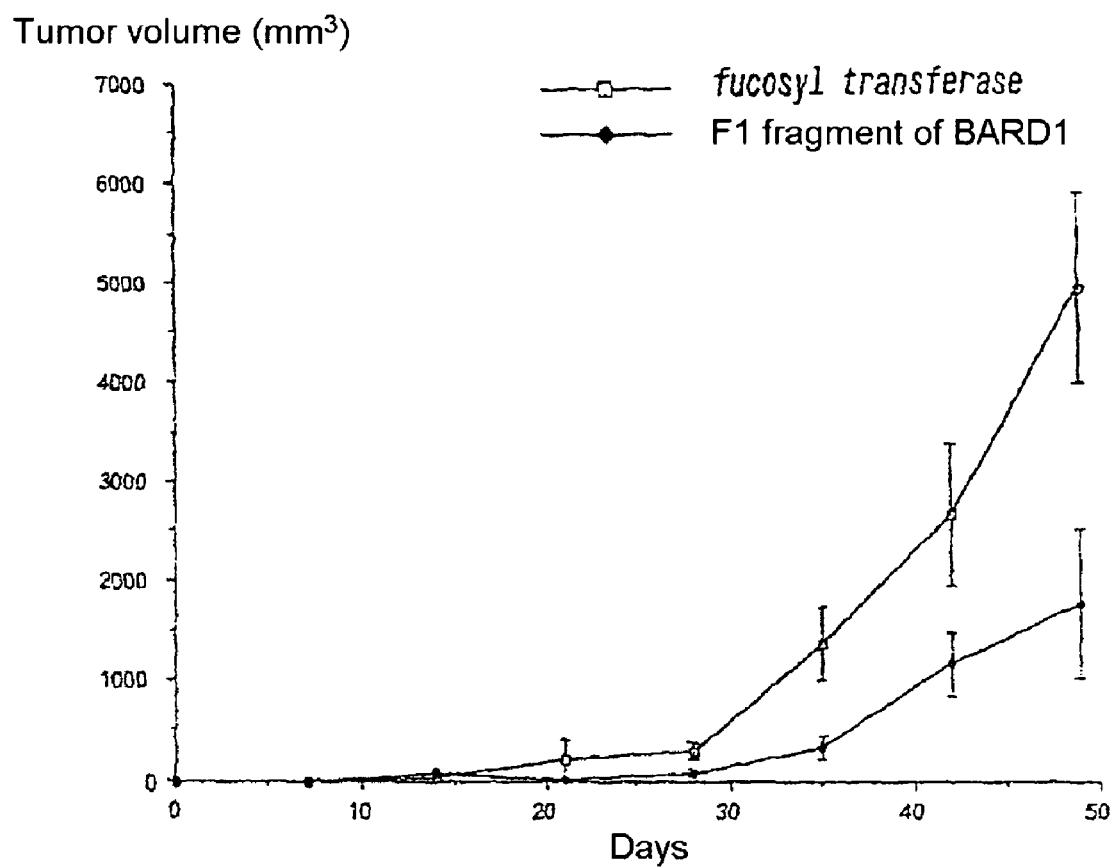

FIG. 4 is a graph representing PROb tumor growth in BDIX rats after vaccination with the F1 fragment of BARD1 or a control protein (fucosyl transferase).

EXAMPLES

Example 1

Identification of a 67 kD Protein as a Product of Cleavage of the BARD1 Protein

Materials and Methods:

Cell Cultures

The REGb rat colon carcinoma cells and PROb rat colon adenocarcinoma cells used are derived from a cell line induced with dimethylhydrazine (Caignard et al., 1985). The 13762 rat breast carcinoma, the SW48 human colon carcinoma and the MCF7 breast carcinoma were obtained from the ECACC. The cells were cultured in monolayer cultures at 37° C. in RMPI 1640 medium (Gibco) with 10% of fetal calf serum and 2 mM of glutamine. The cells were subcultured with 0.025% of trypsin and 0.02% of EDTA.

Immunoscreening and Cloning of the Rat BARD1 cDNA (SEQ ID NO:10)

A cDNA library of the PROb rat carcinoma cell line was constructed in the .lambda.TriplEx expression vector (Clontech). One million plaques were screened with sera from rats vaccinated with apoptotic antibodies and IL-2 (Boisteau et al., 1997). The antibodies against E. coli were removed from the rat antisera by incubating sonicated E. coli bacteria with serum diluted to 1/10 in PBS plus 5% of dehydrated skimmed milk, for 4 hours at ambient temperature, and then centrifuged at 13,000 g for 10 minutes. The 456 base pair insert (fragment F1) was sequenced and the sequence is subjected to analysis on the NCB1 gene bank. It represented a strong homology with the human BARD1 protein. The complete rat BARD1 cDNA (SEQ ID NO:10) was cloned using the PROb cDNA library constructed with the PCR SMART kit from Clontech. The internal primers for the RACE PCR were selected based on the insert cloned according to the manufacturer's instructions.

Cloning of the Human BARD1 cDNA

Three human BARD1 cDNA fragments were amplified from total RNA extracted from SW48 human colon carcinoma cell lines. The fragments, designated A, B and C, were obtained using the following primers: fragment A sense primer R135S/antisense primer B202N (Thai et al., 1998); fragment B, sense primer B202A (Thai et al., 1998), antisense primer: 5' CACCAATGCCTTATGCTGGAGC 3' (SEQ ID NO:2); fragment C, sense primer: 5' GAAGTAGTGACTCCTGAGAAGG 3' SEQ ID NO:3)/antisense primer 5' TCAGCTGTCAAGAGGAAGCAACTC 3' (SEQ ID NO:4). Each fragment was cloned into a PGEM plasmid (Promega), then excised using Not1-Pst1/Pst1-Hind III/Hind III-Bst XI, respectively, purified, and then ligated into the Not1/Bst XI sites of PGEM.

Apoptotic Induction and Purification of Apoptotic Bodies

Apoptosis was induced by treatment with sodium butyrate (NaB). The cells at different stages of confluence were treated in complete medium at 37° C. and with 5 mM of NaB (Sigma)

for various periods of time. The apoptotic bodies were purified as previously described (Gautier et al., 1999):

Production and Purification of F1 Fragments of Rat BARD1

The F1 fragment of rat BARD1 (SEQ ID NO:9) was excised from the plasmid λTriplex of the cDNA library and inserted, in frame, into the Pst1 site of the plasmid pQE32 (Qiagen). The resulting fusion protein, containing a 6xHis tag placed at the N-terminal end of the F1 fragment of BARD1 (SEQ ID NO:9), was expressed in *E. coli*, then purified by affinity chromatography on a Ni-NTA resin using the manufacturer's recommendations for the QIA expressionist kit (Qiagen).

Immunization of the Mice and Production of Monoclonal Antibody

Balb-c mice (Iffa-credo) were given subcutaneous injections of 100 μg of the F1 fragment of rat BARD1 (SEQ ID NO:9) in 0.1 ml of incomplete Freund's adjuvant (Life Technologies) emulsified in 0.1 ml of sterile PBS buffer containing 0.5% of Triton X-100, 3 weeks apart. The splenocytes of a mouse were fused with the SP20 mouse myloma (ECACC) in the presence of polyethylene glycol 1500 (Boehringer Mannheim). The hybridomas were deposited onto 96-well plates in complete medium supplemented with 20% of fetal calf serum, hypoxanthine-aminopterin-thymidine (Sigma) and 1.5 ng/ml of recombinant IL6 (RD Systems). The hybridome supernatants were tested by ELISA using a purified BARD1 F1 fragment (SEQ ID NO:9) as antigen.

Immunoprecipitation

The apoptotic bodies were extracted on ice with 2% of Triton X-100 in PBS supplemented with a cocktail of protease inhibitors free of EDTA (Boehringer Mannheim) for 30 minutes. The extract was centrifuged for 15 minutes at 13,000 g and the supernatant was incubated with rabbit polyclonal antibodies directed against the human BARD1 protein (669D) (SEQ ID NO:1) (Wu et al., 1996 and Jin et al., 1997), diluted to 1/1000. After incubation for 4 hours, with constant stirring, the immunocomplexes were immunoprecipitated by adding 50 μl of anti-rabbit IgG agarose. The immunocomplexes bound to the agarose were washed with PBS containing 1% of Triton X-100 and protease inhibitors and were extracted from the agarose beads by heating in a reducing buffer for electrophoresis and immunoblotting as described below.

Western Blotting

The electrophoresis was carried out under denaturing conditions (SDS PAGE) (Laemmli et al., 1970). The proteins were transferred onto a 0.45 μm PVDF filter (Millipore) and brought into contact with primary antibodies. Secondary antibodies conjugated to horseradish peroxidase were used, diluted to 1/15000 (Sigma). The immunocomplexes were visualized by chemiluminescence using a Super Signal kit (Pierce).

Coupled in vitro Transcription/Translation and Determination of Cleavage of the Protein in vitro:

The human BARD1 protein (SEQ ID NO:1), labeled with $^{35}$S-methionine, was transcribed and translated in vitro using the TNT coupled reticulocytes lysate system kit (Promega). 1 μg of plasmid was used in a reaction medium for the transcription and the translation, containing 4 μl of $^{35}$S-methionine (NEN). For the in vitro cleavage, 2 μl of transcription/translation products were incubated with apoptotic or nonapoptotic cell extracts prepared in a DIV buffer (20 mM HEPES. PH 7.5, 10 mM NaCl, 1.5 mM MgCl$_2$, 0.1% SB14, 0.5 mM PMSF) at 37° C. for the period of time indicated. The hydrolysis products were then separated by SDS-PAGE and revealed by autoradiography using the phosphorimager 445SI (Molecular Dynamics). Inhibition of the cleavage was evaluated by adding caspase inhibitors or a proteasome inhibitor (lactacystine) (Calbiochem) or the calpain inhibitor I(ALLnL) (Chemicon).

Cell Cycle Synchronization

The SW48 cells were arrested in $G_0$ by contact inhibition in 175 cm$^2$ flasks. After confluencing for 3 days, the cells were split 1:10 in 75 cm$^2$ flasks at a concentration of 3×10$^6$ cells per flask. 12, 20, 28, 36 and 44 hours after seeding, the cells were treated with 5 mM of NaB for 24 hours and collected. To determine the cell cycle distribution at each time, the content of each flask was subjected to trypsinization, washed three times in 10 ml of ice-cold PBS, and fixed with 1 ml of ice-cold 70% ethanol, added dropwise, for 16 hours at −20° C. The fixed cells were pelletted, resuspended in 500 μl of PC buffer (96% 0.2M Na$_2$HPO$_4$, 4% 0.1M citric acid, pH 7.8) and left at ambient temperature for 30 minutes. They were then washed and resuspended in 500 μl of propidium iodide in a staining solution (PBS, 0.12% Triton X-100, 0.12 mM EDTA, 100 μg/ml RNase A), incubated for 30 minutes at 37° C. and analyzed on a FACScan (flow cytometer) (Beckton Dickinson). To determine the cleavage of the protein in vitro, the cells were scraped and the cell extracts were prepared as previously described.

Results

Cloning of the cDNA Encoding the 67 kD Protein

Figure 1:
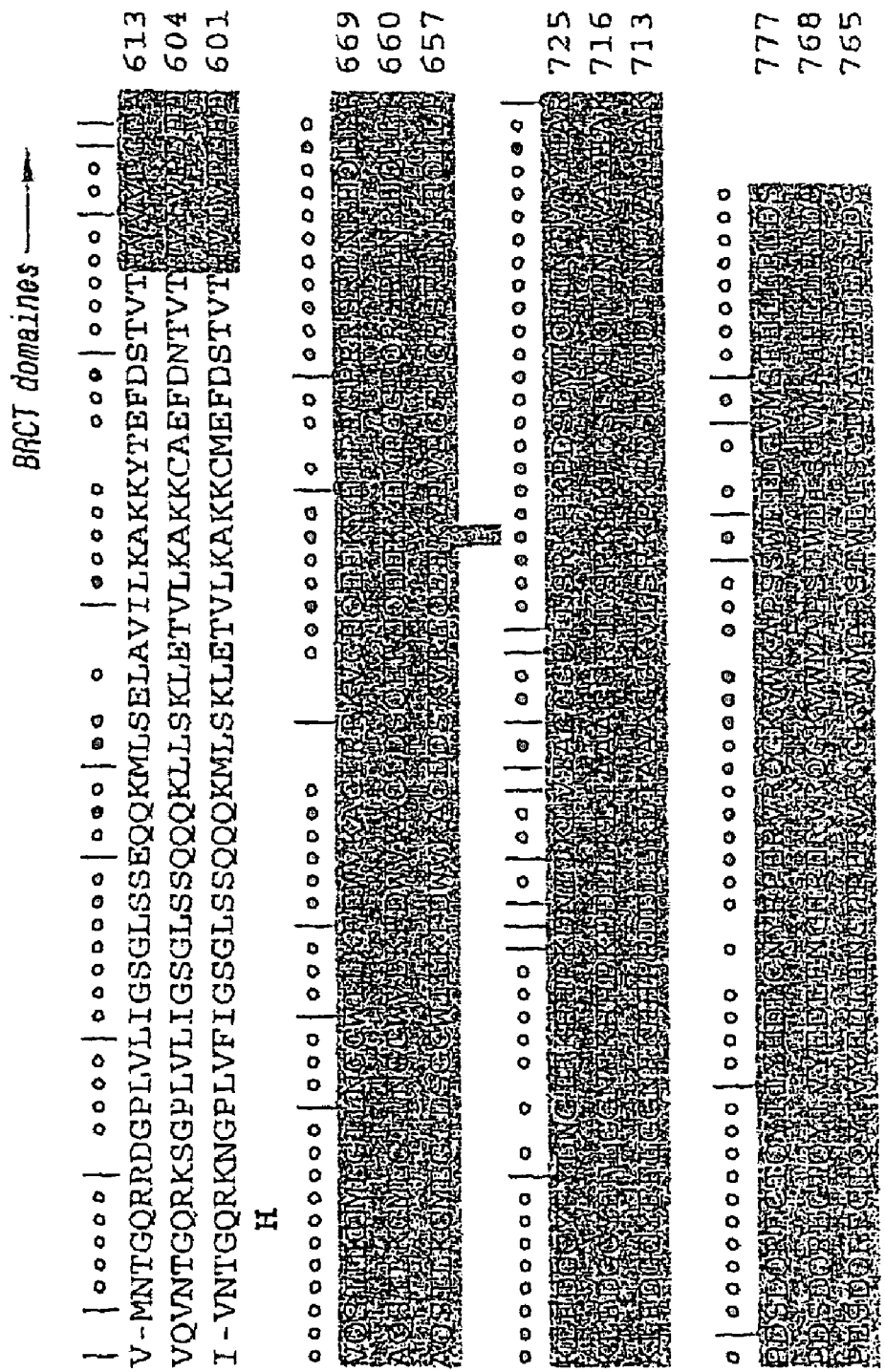

The immunoscreening of the λTriplEx cDNA library with sera from rats treated for a carcinoma with apoptotic bodies/IL-2 led to the identification of a positive insert of 456 pairs of the rat BARD1 gene (F1 fragment) (SEQ ID NO:10). This fragment extends between amino acids 460 to 611 (FIG. 1) (SEQ ID NO:9). Table 1 below gives the percentage homology between the rat (SEQ ID NO:6), human (SEQ ID NO:1) and mouse (SEQ ID NO:5) BARD1 protein.

Percentage Homology Between the Rat, Human and Mouse BARD1 Protein

| Species | Total | RING | Ankyrin | BRCT |
|---|---|---|---|---|
| Rat/mouse | 87.9 | 95.5 | 93.9 | 94.2 |
| Rat/human | 64.8 | 86.6 | 90.9 | 80.3 |
| Mouse/human | 67.5 | 86.6 | 90.9 | 79.7 |

The 67 kD Protein is a Fragment of BARD1

Figure 2:
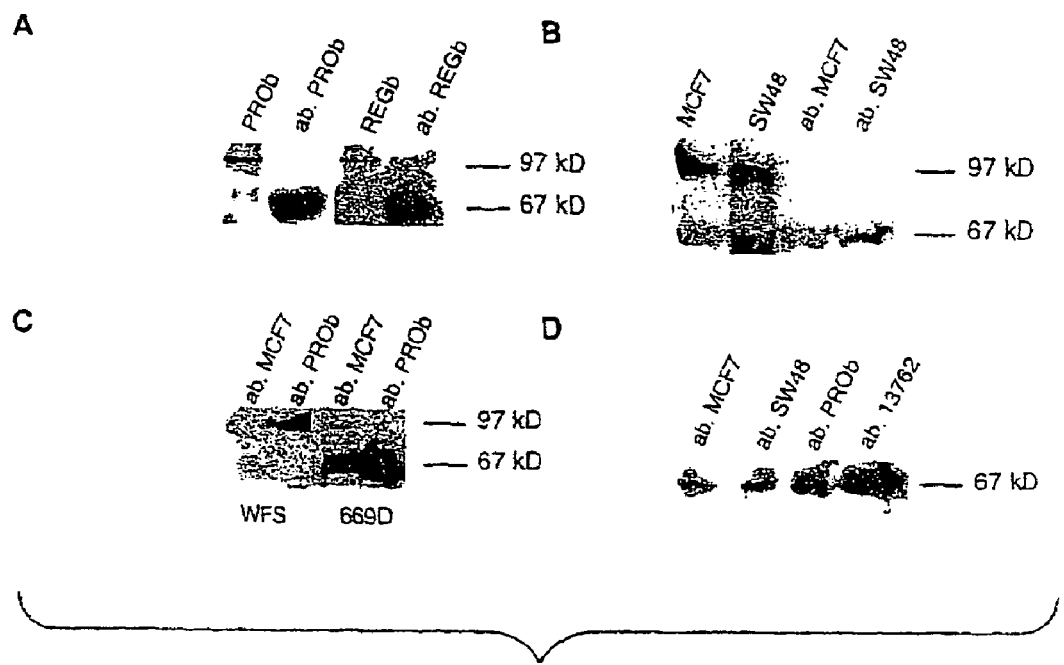
FIG. 2A represents a Western blotting analysis of proteins of rat and human carcinoma cells and of their apoptotic bodies revealed with a rat anti-BARD1 monoclonal antibody 6D10.
FIG. 2B represents the same type of analysis, with revelation using an anti-human polyclonal antibody 669D. It should be noted that a.b. signifies apoptotic body.
FIG. 2C represents a Western Blotting analysis of apoptotic body proteins, first carried out using an anti-mouse BARD1 polyclonal antibody WFS. The immunocomplexes are dissociated using the chemicon kit and the filter is further subjected to an anti-human BARD1 antibody 669D.
FIG. 2D represents an immunoprecipitation of lysates of apoptotic body derived from several carcinoma cells, with revelations in an anti-human BARD1 antibody 669D. The precipitate was subjected to electrophoresis and then immunoblotting was carried out with serum from rats immunized with PROb apoptotic bodies, diluted to 1/250.

In order to be able to prove the identity of the 67 kD protein, as a fragment of BARD1, the authors of the invention determined its expression in the tumor cells and the apoptotic bodies. For this purpose, they produce monoclonal antibodies (clone 6D10) against the F1 fragment (SEQ ID NO:9). When it was tested on PROb and REGb rat carcinoma cells, the monoclonal antibodies 6D10 recognized a 97 kD protein, but also a band of approximately 67 kD in the apoptotic bodies derived from the cells after treatment with sodium butyrate (FIG. 2A). This result was confirmed using a polyclonal antibody 669D (Wu et al., 1996 and Jin et al., 1997) against the human BARD1 protein (SEQ ID NO:1). Treatment of SV48 human colon cells or MCF7 mammary gland cells with sodium butyrate led to a similar result after immunoblotting with a polyclonal antibody 669D (FIG. 2B). Finally, immunoprecipitation of BARD1 from apoptotic bodies derived from rat human carcinomas, with the polyclonal antibody 669D, followed by immunoblotting with a treated rat serum, made it possible to detect a 67 kD protein (FIG. 2D). This set of results proves the identity of the 67 kD protein as a fragment of BARD1.

BARD1 is Cleaved During Apoptosis

When the apoptotic bodies derived either from human MCF7 carcinomas or from rat PROb carcinoma were incubated, on the same membrane, successively with the anti-human BARD1 polyclonal antibody 669D or the antibody WFS against the N-terminal portion of the mouse BARD1 protein (amino acids 101-114 of SEQ ID NO:5) (Irminger-Finger 1988), the authors of the invention observe that the antibody WFS did not recognize the 67 kD molecule, while the antibody 669D recognized the 67 kD molecule in each of the types of apoptotic body (FIG. 2C). This strongly suggests that the BARD1 cleavage site is located in the N-terminal portion, but downstream of the RING domain (amino acids 40-84 of SEQ ID NO:1, SEQ ID NO:5, and SEQ ID NO:6, FIG. 1) essential for the interaction of the BARD1 and BRCA1 proteins (Wu et al., 1996).

The Cleavage of BARD1 During Apoptosis is Cell Cycle Dependent.

The authors of the invention examined the effect of the treatment with NaB for the cleavage of BARD1 in the adherent SW48 cells or in the apoptotic bodies collected from the supernatant. FIG. 3A shows that the adherent cell lysates completely cleave the radiolabeled human BARD1 protein (SEQ ID NO:1) after 4 hours of incubation, since the full length human BARD1 protein (SEQ ID NO:1) completely disappears and the 67 kD protein appears. However, incubation with lysates of apoptotic bodies has no effect on the hydrolysis of hBARD1 (SEQ ID NO:1). These results indicate that the proteolytic activity involved in the cleavage of BARD1 intervenes before the ultimate step of apoptosis which leads to the formation of apoptotic bodies and to cell detachment. Analysis of the kinetics leading to the hydrolysis of hBARD1 (SEQ ID NO:1) with lysates of the SW48 adherent cells treated for 48 hours with 5 mM of NaB showed that the cleavage is finished after one hour (FIG. 3B). Further analysis of the kinetic induction of this cleavage by NaB showed that the p67 protein appeared after 4 hours of treatment of the cells with NaB and that the cleavage was virtually complete after 12 hours. Interestingly, the hydrolysis of hBARD1 (SEQ ID NO:1) is regulated in a cell cycle-dependent manner, with a predominance during the $G_0/G_1$ phase. This was demonstrated by addition of NaB 32 hours after rupturing of the cells, a stage at which 80% of the cells were in $G_0/G_1$ phase and only 5% in G2/M phase, which led to complete conversion of hBARD1 (SEQ ID NO:1) to p67.

Example 2

Cleavage with Calpains

Materials and Methods

Determination of the Caspase Activity

For assaying the caspase activity, 10 μg of cell extracts were diluted in 5 μl of DIV buffer:

Acetyl-Asp-Glu-Val-Asp-7-amino-4-methylcoumarin (Ac-DEVD-AMC), acetyl-Val-Glu-Ile-Asp-7-amino-4-methylcoumarin (Ac-VEID-AMC) and acetyl-Ile-Glu-Ile-Asp-7-amino-4-methylcoumarin (Ac-IEID-AMC) (Bachem), substrates for caspases 3,6 and 8, respectively, were added at a final concentration of 50 μM. The cleavage activity was controlled on Fluorolite 1000 (Dynatech laboratories).

Cellular Fraction

The cells were cultured in 75 cm² flasks, trypsinized, and resuspended in 100 μl of CEB buffer (50 mM HEPES pH 7.4, 50 mM $MgCl_2$, 1 mM DTT, 10 μM cytochalasin B). The resuspended cells were left on ice for 30 minutes and then homogenized with 50 strokes of a Dounce homogenizer, and cooled in ice. The nucleic fraction was prepared by centrifugation at 800×g for 10 minutes at 4° C. The pellet was resuspended in a CEB buffer and stored at −80° C. The mitochondrial and post-mitochondrial fractions were obtained after centrifugation at 13,000×g for 10 minutes at 4° C. Both the mitochondrial pellet resuspended in CEB and the post-mitochondrial fractions were divided into aliquot fractions and stored at −80° C.

Results

To define the proteolytic activity responsible for the cleavage of hBARD1 (SEQ ID NO:1), various preparations of cell extracts from SW48 cells treated with NAB were tested. It appears that both the nuclear preparations and the mitochondrial preparations were capable of cleaving hBARD1 (SEQ ID NO:1). The supernatant at 13,000×g of the organelle preparation had no effect.

The cascade of proteases which are effectors of the apoptotic process comprises cysteine proteases such as caspases or calpains. The authors of the invention then determined the caspase activities during the treatment of the SW48 cells with NaB, using specific substrates, and found that the activities of caspases 3, 6 and 8 gradually increased, caspase 3 being the most active after 6 hours and 12 hours of NaB treatment. The use of peptide inhibitors for the caspases showed that benzyloxycarbonyl-Val-Ala-Asp-fluoromethylketone (Z-VAD-fmk), a caspase inhibitor, slightly inhibited the hydrolysis of hBARD1 (SEQ ID NO:1) at high concentration (100 μM). On the other hand, the inhibitors specific for caspase 3, benzyloxycarbonyl-Asp-Glu-Val-Asp-fluoromethylketone(Z-DEVD-fmk) (SEQ ID NO:11) or for caspase 6, benzyloxycarbonyl-Val-Glu-Ile-Asp-fluoromethyl ketone (Z-VEID-fmk) (SEQ ID NO:12), had no effect. This phenomenon was confirmed by the fact that purified caspase 3 had no effect on the hydrolysis of hBARD1 (SEQ ID NO:1). These results clearly show that hBARD1 (SEQ ID NO:1) is not a direct substrate for caspases. In addition, lactacystine, a proteasome inhibitor, does not block the proteolysis of hBARD1 (SEQ ID NO:1), even at concentrations of 100 μm, this excluding the possibility of the proteasome being involved in this mechanism.

A certain number of proteins which had degraded during apoptosis are targets for calpains. A possible mechanism for the activation of calpains involves the cleavage of a calpain inhibitor in vivo, calpastatin (DeMartino et al., 1984). The results of the authors of the invention show, firstly, that calpastatin was completely cleaved in the SW48 cells after 12 hours of treatment with NaB and, secondly, that the calpain inhibitor I, ALLnL, and EGTA strongly inhibited the hydrolysis of hBARD1 (SEQ ID NO:1) in a dose-dependent manner. This set of results strongly suggests that the BARD1 protein is hydrolyzed by calpains.

Example 3

Purification of the Cleaved BARD1 Protein

Production of Antibodies Specific for the Translated Protein

Poly- and monoclonal antibodies directed against peptide sequences are located at the N- and C-terminal ends of the truncated proteins are produced:

against peptide 1 corresponding to amino acids 255 to 265 of the human BARD1 protein (SEQ ID NO:1);

against peptide 2 corresponding to amino acids 527 to 540 of the human BARD1 protein (SEQ ID NO:1).

The peptides were coupled to KLH. Each rabbit was given three injections of 200 μg of each peptide, 15 days apart. A fourth injection was given three weeks after the last injection. The production of antibodies was tested on the serum of the rabbit by the ELISA technique using the free peptides as antigen.

The titers of the sera obtained were high ($1/16000$). In addition, no cross reactivity was observed between the sera of the two peptides.

Purification of the Cleaved BARD1 Protein

These antibodies allow the authors of the invention to purify the truncated protein, by affinity chromatography, either from apoptotic bodies or tumor cells or from the whole BARD1 protein produced and cleaved in vitro as described above.

The purification is carried out using standard techniques of affinity chromatography. The purified fractions are identified by western blotting with the antibodies produced.

Example 4

Vaccination of the Rats with the Truncated BARD1 Protein (SEQ ID NO:9)

Materials and Methods

Two groups of BDIX rats were given three weekly intraplantar injections of 100 μg of F1 fragment (amino acids 460-611) of BARD1 (SEQ ID NO:9) or of a controlled protein (fucosyl transferase) purified under the same conditions as the F1 fragment. The proteins were emulsified in 100 μl of complete Freund's adjuvant. Two weeks after the final immunization, the rat colon tumor cells (PROb, $50 \times 10^3$/rat) were injected subcutaneously and the volume of the PROb tumors was estimated.

Result

A slowing down of tumor growth is observed, thus demonstrating the protective effect of a vaccination with a BARD1 fragment derived from the 67 kD form (FIG. 4) (each point represents the mean of the tumor volumes measured on 6 rats, with the standard deviation).

BIBLIOGRAPHIC REFERENCES

Benoit et al., PNAS USA, 79, 917-921 (1982).

Boisteau et al., Apoptosis induced by sodium butyrate treatment increases immunogenicity of a rat colon tumor cell line. Apoptosis, 2:403-412, 1997.

Caignard et al., Interaction between two cellular subpopulations of a rat colonic carcinoma when inoculated to syngeneic host. Int. J. Cancer., 36:273-279, 1985.

G. N. Demartino, and D. E. Croall Purification and characterization of a protein inhibitor of calcium-dependent protease from rat liver. Arch. Biochem. Biophys., 232; 713-720, 1984.

Gautier et al., Production and characterization of a monoclonal antibody specific for apoptotic bodies derived from several tumor cell lines. J. Immunol. Meth., 228; 49-58, 1999.

Irminger-Finger et al., In vitro repression of Brca1-associated RING domain gene, Bard1, induces phenotypic changes in mammary epithelial cells. J. Cell Biol.: 143: 1329-1339, 1998.

Jin et al., Cell cycle-dependent colocalization of BARD1 and BRCA1 proteins in discrete nuclear domains. Proc. Natl. Acad. Sci. USA., 94: 12075-12080, 1997.

Köhler and Milstein, Nature, 256, 495-497, (1975). Laemmli et al., Cleavage of structural proteins during the assembly of the head of bacteriophage T4. Nature, 277:680-685, 1970.

U. K. Laemmli, Cleavage of structural proteins during the assembly of the head of bacteriophage T4, Nature, 277: 680-685, 1970.

Thai, et al., Mutation in the BRCA1-associated RING domain (BARD1) gene in primary breast ovarian and uterine cancers. Human Mol. Gen., 7: 195-202, 1998.

Wu et al., Identification of a RING protein that can interact in vivo with the BRCA1 gene product. Nature Gen., 14: 430-440, 1996.

SEQUENCE LISTING

<160> NUMBER OF SEQ ID NOS: 4

<210> SEQ ID NO 1
<211> LENGTH: 777
<212> TYPE: PRT
<213> ORGANISM: Homo sapiens

<400> SEQUENCE: 1

```
Met Pro Asp Asn Arg Gln Pro Arg Asn Arg Gln Pro Arg Ile Arg Ser
 1               5                  10                  15

Gly Asn Glu Pro Arg Ser Ala Pro Ala Met Glu Pro Asp Gly Arg Gly
            20                  25                  30

Ala Trp Ala His Ser Arg Ala Ala Leu Asp Arg Leu Glu Lys Leu Leu
        35                  40                  45

Arg Cys Ser Arg Cys Thr Asn Ile Leu Arg Glu Pro Val Cys Leu Gly
    50                  55                  60

Gly Cys Glu His Ile Phe Cys Ser Asn Cys Val Ser Asp Cys Ile Gly
```

-continued

```
                65                  70                  75                  80
Thr Gly Cys Pro Val Cys Tyr Thr Pro Ala Trp Ile Gln Asp Leu Lys
                    85                  90                  95
Ile Asn Arg Gln Leu Asp Ser Met Ile Gln Leu Cys Ser Lys Leu Arg
                    100                 105                 110
Asn Leu Leu His Asp Asn Glu Leu Ser Asp Leu Lys Glu Asp Lys Pro
                    115                 120                 125
Arg Lys Ser Leu Phe Asn Asp Ala Gly Asn Lys Lys Asn Ser Ile Lys
                    130                 135                 140
Met Trp Phe Ser Pro Arg Ser Lys Lys Val Arg Tyr Val Val Ser Lys
145                 150                 155                 160
Ala Ser Val Gln Thr Gln Pro Ala Ile Lys Lys Asp Ala Ser Ala Gln
                    165                 170                 175
Gln Asp Ser Tyr Glu Phe Val Ser Pro Ser Pro Ala Asp Val Ser
                    180                 185                 190
Glu Arg Ala Lys Lys Ala Ser Ala Arg Ser Gly Lys Lys Gln Lys Lys
                    195                 200                 205
Lys Thr Leu Ala Glu Ile Asn Gln Lys Trp Asn Leu Glu Ala Glu Lys
                    210                 215                 220
Glu Asp Gly Glu Phe Asp Ser Lys Glu Ser Lys Gln Lys Leu Val
225                 230                 235                 240
Ser Phe Cys Ser Gln Pro Ser Val Ile Ser Pro Gln Ile Asn Gly
                    245                 250                 255
Glu Ile Asp Leu Leu Ala Ser Gly Ser Leu Thr Glu Ser Glu Cys Phe
                    260                 265                 270
Gly Ser Leu Thr Glu Val Ser Leu Pro Leu Ala Glu Gln Ile Glu Ser
                    275                 280                 285
Pro Asp Thr Lys Ser Arg Asn Glu Val Val Thr Pro Glu Lys Val Cys
                    290                 295                 300
Lys Asn Tyr Leu Thr Ser Lys Ser Leu Pro Leu Glu Asn Asn Gly
305                 310                 315                 320
Lys Arg Gly His His Asn Arg Leu Ser Ser Pro Ile Ser Lys Arg Cys
                    325                 330                 335
Arg Thr Ser Ile Leu Ser Thr Ser Gly Asp Phe Val Lys Gln Thr Val
                    340                 345                 350
Pro Ser Glu Asn Ile Pro Leu Pro Glu Cys Ser Ser Pro Pro Ser Cys
                    355                 360                 365
Lys Arg Lys Val Gly Gly Thr Ser Gly Ser Lys Asn Ser Asn Met Ser
                    370                 375                 380
Asp Glu Phe Ile Ser Leu Ser Pro Gly Thr Pro Pro Ser Thr Leu Ser
385                 390                 395                 400
Ser Ser Ser Tyr Arg Arg Val Met Ser Ser Pro Ser Ala Met Lys Leu
                    405                 410                 415
Leu Pro Asn Met Ala Val Lys Arg Asn His Arg Gly Glu Thr Leu Leu
                    420                 425                 430
His Ile Ala Ser Ile Lys Gly Asp Ile Pro Ser Val Glu Tyr Leu Leu
                    435                 440                 445
Gln Asn Gly Ser Asp Pro Asn Val Lys Asp His Ala Gly Trp Thr Pro
                    450                 455                 460
Leu His Glu Ala Cys Asn His Gly His Leu Lys Val Val Glu Leu Leu
465                 470                 475                 480
Leu Gln His Lys Ala Leu Val Asn Thr Thr Gly Tyr Gln Asn Asp Ser
                    485                 490                 495
```

-continued

Pro Leu His Asp Ala Ala Lys Asn Gly His Val Asp Ile Val Lys Leu
        500                 505                 510

Leu Leu Ser Tyr Gly Ala Ser Arg Asn Ala Val Asn Ile Phe Gly Leu
        515                 520                 525

Arg Pro Val Asp Tyr Thr Asp Asp Glu Ser Met Lys Ser Leu Leu Leu
        530                 535                 540

Leu Pro Glu Lys Asn Glu Ser Ser Ser Ala Ser His Cys Ser Val Met
545                 550                 555                 560

Asn Thr Gly Gln Arg Arg Asp Gly Pro Leu Val Leu Ile Gly Ser Gly
            565                 570                 575

Leu Ser Ser Glu Gln Gln Lys Met Leu Ser Glu Leu Ala Val Ile Leu
        580                 585                 590

Lys Ala Lys Lys Tyr Thr Glu Phe Asp Ser Thr Val Thr His Val Val
        595                 600                 605

Val Pro Gly Asp Ala Val Gln Ser Thr Leu Lys Cys Met Leu Gly Ile
    610                 615                 620

Leu Asn Gly Cys Trp Ile Leu Lys Phe Glu Trp Val Lys Ala Cys Leu
625                 630                 635                 640

Arg Arg Lys Val Cys Glu Gln Glu Lys Tyr Glu Ile Pro Glu Gly
            645                 650                 655

Pro Arg Ser Arg Leu Asn Arg Glu Gln Leu Leu Pro Lys Leu Phe
            660                 665                 670

Asp Gly Cys Tyr Phe Tyr Leu Trp Gly Thr Phe Lys His His Pro Lys
        675                 680                 685

Asp Asn Leu Ile Lys Leu Val Thr Ala Gly Gly Gly Gln Ile Leu Ser
    690                 695                 700

Arg Lys Pro Lys Pro Asp Ser Asp Val Thr Gln Thr Ile Asn Thr Val
705                 710                 715                 720

Ala Tyr His Ala Arg Pro Asp Ser Asp Gln Arg Phe Cys Thr Gln Tyr
            725                 730                 735

Ile Ile Tyr Glu Asp Leu Cys Asn Tyr His Pro Glu Arg Val Arg Gln
        740                 745                 750

Gly Lys Val Trp Lys Ala Pro Ser Ser Trp Phe Ile Asp Cys Val Met
        755                 760                 765

Ser Phe Glu Leu Leu Pro Leu Asp Ser
770                 775

<210> SEQ ID NO 2
<211> LENGTH: 22
<212> TYPE: DNA
<213> ORGANISM: artificial sequence
<220> FEATURE:
<223> OTHER INFORMATION: Artificial sequence description:
      oligonucleotide (PCR primer)

<400> SEQUENCE: 2
caccaatgcc ttatgctgga gc                                              22

<210> SEQ ID NO 3
<211> LENGTH: 22
<212> TYPE: DNA
<213> ORGANISM: Artificial sequence
<220> FEATURE:
<223> OTHER INFORMATION: Artificial sequence description:
      oligonucleotide (PCR primer)

<400> SEQUENCE: 3

```
gaagtagtga ctcctgagaa gg                                          22
```

```
<210> SEQ ID NO 4
<211> LENGTH: 24
<212> TYPE: DNA
<213> ORGANISM: Artificial sequence
<220> FEATURE:
<223> OTHER INFORMATION: Artificial sequence description:
      oligonucleotide (PCR primer)

<400> SEQUENCE: 4
tcagctgtca agaggaagca actc                                        24
```

The invention claimed is:

1. An isolated polypeptide fragment which has a molecular weight of approximately 67 kD, wherein the fragment consists essentially of 505 to 525 contiguous amino acids from amino acid position 252 to amino acid position 777 of the C-terminal end of BARD 1 of SEQ ID NO: 1.

2. An isolated nucleic acid consisting essentially of a nucleotide sequence encoding the polypeptide fragment of claim 1.

3. A cloning and/or expression vector comprising the nucleic acid sequence of claim 2.

4. An isolated host cell transfected with a vector according to claim 3.

5. A method of producing a polypeptide fragment which has a molecular weight of approximately 67 kD, wherein the fragment consists of 505 to 525 contiguous amino acids, from amino acid position 252 to amino acid position 777 of the C-terminal end of BARD 1 of SEQ ID NO: 1 which method comprises culturing an isolated host cell transfected with an expression vector of claim 3 under conditions allowing expression of the protein.

6. A composition comprising a polypeptide fragment according to claim 1, in combination with a pharmaceutically acceptable vehicle.

7. A composition comprising a nucleic acid according to claim 2, in combination with a pharmaceutically acceptable vehicle.

8. A method for eliciting an antibody response to a BARD 1 protein which method comprises administering a polypeptide fragment of claim 1 to a subject.

9. An isolated polypeptide fragment consisting essentially of residues 460-611 from the C-terminal end of BARD1 of SEQ ID NO: 1.

10. An isolated nucleic acid consisting essentially of a nucleotide sequence encoding the polypeptide fragment of claim 9.

11. A cloning and/or expression vector comprising the nucleic acid sequence of claim 10.

12. An isolated host cell transfected with a vector according to claim 11.

13. A method of producing a polypeptide consisting of residues 460-611 from the C-terminal end of BARD1 of SEQ ID NO: 1 which method comprises culturing an isolated host cell transfected with an expression vector of claim 11 under conditions allowing expression of the protein.

14. A composition comprising a polypeptide fragment according to claim 9, in combination with a pharmaceutically acceptable vehicle.

15. A composition comprising a nucleic acid according to claim 10, in combination with a pharmaceutically acceptable vehicle.

16. A method for inhibiting tumor cell growth which method comprises administering a composition according to claim 15 to a subject bearing a tumor.

17. An isolated C-terminal polypeptide fragment consisting essentially of 151 contiguous amino acids from residues 460-611 from the C-terminal end of BARD1 of SEQ ID NO: 1, and wherein the polypeptide fragment inhibits tumor cell growth.

18. A method for eliciting an antibody response to a BARD1 protein which method comprises administering a polypeptide fragment of claim 9 to a subject.

19. A method for eliciting an antibody response to a BARD1 protein which method comprises administering a composition of claim 14 to a subject.

20. A method for inhibiting tumor cell growth which method comprises administering an isolated C-terminal polypeptide fragment consisting essentially of residues 460-611 from the C-terminal end of SEQ ID NO: 1 (BARD 1) and wherein the polypeptide fragment inhibits tumor cell growth in a subject bearing a tumor.

* * * * *

UNITED STATES PATENT AND TRADEMARK OFFICE
CERTIFICATE OF CORRECTION

PATENT NO. : 7,566,764 B2
APPLICATION NO. : 10/363285
DATED : July 28, 2009
INVENTOR(S) : Fabien Gautier et al.

It is certified that error appears in the above-identified patent and that said Letters Patent is hereby corrected as shown below:

Column 1,
Line 38, "the the polypeptide" should read --the polypeptide--.

Columns 11-18,
Delete sequence listing and replace with attached sequence listing.

Signed and Sealed this

Twenty-ninth Day of December, 2009

David J. Kappos
*Director of the United States Patent and Trademark Office*

SEQUENCE LISTING

<110> Gautier, Fabien
      Harb, Jean
      Meflah, Khaled
      Irminger-Finger, Irmgard

<120> TRUNCATED BARD1 PROTEIN, AND ITS DIAGNOSTIC AND THERAPEUTIC USES

<130> 21051/000M621-US0

<140> 10/363,285
<141> 2003-02-27

<150> PCT/FR01/02731
<151> 2001-09-03

<150> FR 00/11207
<151> 2000-09-01

<160> 12

<170> PatentIn version 3.3

<210> 1
<211> 777
<212> PRT
<213> Homo sapiens

<400> 1

```
Met Pro Asp Asn Arg Gln Pro Arg Asn Arg Gln Pro Arg Ile Arg Ser
1               5                   10                  15

Gly Asn Glu Pro Arg Ser Ala Pro Ala Met Glu Pro Asp Gly Arg Gly
            20                  25                  30

Ala Trp Ala His Ser Arg Ala Ala Leu Asp Arg Leu Glu Lys Leu Leu
        35                  40                  45

Arg Cys Ser Arg Cys Thr Asn Ile Leu Arg Glu Pro Val Cys Leu Gly
    50                  55                  60

Gly Cys Glu His Ile Phe Cys Ser Asn Cys Val Ser Asp Cys Ile Gly
65                  70                  75                  80

Thr Gly Cys Pro Val Cys Tyr Thr Pro Ala Trp Ile Gln Asp Leu Lys
                85                  90                  95

Ile Asn Arg Gln Leu Asp Ser Met Ile Gln Leu Cys Ser Lys Leu Arg
            100                 105                 110

Asn Leu Leu His Asp Asn Glu Leu Ser Asp Leu Lys Glu Asp Lys Pro
        115                 120                 125
```

Arg Lys Ser Leu Phe Asn Asp Ala Gly Asn Lys Asn Ser Ile Lys
    130             135             140

Met Trp Phe Ser Pro Arg Ser Lys Lys Val Arg Tyr Val Val Ser Lys
145             150             155             160

Ala Ser Val Gln Thr Gln Pro Ala Ile Lys Lys Asp Ala Ser Ala Gln
                165             170             175

Gln Asp Ser Tyr Glu Phe Val Ser Pro Ser Pro Ala Asp Val Ser
            180             185             190

Glu Arg Ala Lys Lys Ala Ser Ala Arg Ser Gly Lys Lys Gln Lys Lys
        195             200             205

Lys Thr Leu Ala Glu Ile Asn Gln Lys Trp Asn Leu Glu Ala Glu Lys
    210             215             220

Glu Asp Gly Glu Phe Asp Ser Lys Glu Ser Lys Gln Lys Leu Val
225             230             235             240

Ser Phe Cys Ser Gln Pro Ser Val Ile Ser Ser Pro Gln Ile Asn Gly
            245             250             255

Glu Ile Asp Leu Leu Ala Ser Gly Ser Leu Thr Glu Ser Glu Cys Phe
            260             265             270

Gly Ser Leu Thr Glu Val Ser Leu Pro Leu Ala Glu Gln Ile Glu Ser
        275             280             285

Pro Asp Thr Lys Ser Arg Asn Glu Val Val Thr Pro Glu Lys Val Cys
    290             295             300

Lys Asn Tyr Leu Thr Ser Lys Lys Ser Leu Pro Leu Glu Asn Asn Gly
305             310             315             320

Lys Arg Gly His His Asn Arg Leu Ser Ser Pro Ile Ser Lys Arg Cys
            325             330             335

Arg Thr Ser Ile Leu Ser Thr Ser Gly Asp Phe Val Lys Gln Thr Val
            340             345             350

Pro Ser Glu Asn Ile Pro Leu Pro Glu Cys Ser Ser Pro Pro Ser Cys
        355             360             365

Lys Arg Lys Val Gly Gly Thr Ser Gly Ser Lys Asn Ser Asn Met Ser
    370             375             380

Asp Glu Phe Ile Ser Leu Ser Pro Gly Thr Pro Pro Ser Thr Leu Ser
385             390             395             400

Ser Ser Ser Tyr Arg Arg Val Met Ser Ser Pro Ser Ala Met Lys Leu
            405             410             415

Leu Pro Asn Met Ala Val Lys Arg Asn His Arg Gly Glu Thr Leu Leu
        420             425             430

His Ile Ala Ser Ile Lys Gly Asp Ile Pro Ser Val Glu Tyr Leu Leu
        435             440             445

Gln Asn Gly Ser Asp Pro Asn Val Lys Asp His Ala Gly Trp Thr Pro
450             455             460

Leu His Glu Ala Cys Asn His Gly His Leu Lys Val Val Glu Leu Leu
465             470             475             480

Leu Gln His Lys Ala Leu Val Asn Thr Thr Gly Tyr Gln Asn Asp Ser
            485             490             495

Pro Leu His Asp Ala Ala Lys Asn Gly His Val Asp Ile Val Lys Leu
        500             505             510

Leu Leu Ser Tyr Gly Ala Ser Arg Asn Ala Val Asn Ile Phe Gly Leu
    515             520             525

Arg Pro Val Asp Tyr Thr Asp Asp Glu Ser Met Lys Ser Leu Leu Leu
530             535             540

Leu Pro Glu Lys Asn Glu Ser Ser Ala Ser His Cys Ser Val Met
545             550             555             560

Asn Thr Gly Gln Arg Arg Asp Gly Pro Leu Val Leu Ile Gly Ser Gly
            565             570             575

Leu Ser Ser Glu Gln Gln Lys Met Leu Ser Glu Leu Ala Val Ile Leu
        580             585             590

Lys Ala Lys Lys Tyr Thr Glu Phe Asp Ser Thr Val Thr His Val Val
        595             600             605

Val Pro Gly Asp Ala Val Gln Ser Thr Leu Lys Cys Met Leu Gly Ile
    610             615             620

Leu Asn Gly Cys Trp Ile Leu Lys Phe Glu Trp Val Lys Ala Cys Leu
625             630             635             640

```
Arg Arg Lys Val Cys Glu Gln Glu Glu Lys Tyr Glu Ile Pro Glu Gly
                645                 650                 655

Pro Arg Arg Ser Arg Leu Asn Arg Glu Gln Leu Leu Pro Lys Leu Phe
            660                 665                 670

Asp Gly Cys Tyr Phe Tyr Leu Trp Gly Thr Phe Lys His His Pro Lys
            675                 680                 685

Asp Asn Leu Ile Lys Leu Val Thr Ala Gly Gly Gly Gln Ile Leu Ser
            690                 695                 700

Arg Lys Pro Lys Pro Asp Ser Asp Val Thr Gln Thr Ile Asn Thr Val
705                 710                 715                 720

Ala Tyr His Ala Arg Pro Asp Ser Asp Gln Arg Phe Cys Thr Gln Tyr
            725                 730                 735

Ile Ile Tyr Glu Asp Leu Cys Asn Tyr His Pro Glu Arg Val Arg Gln
            740                 745                 750

Gly Lys Val Trp Lys Ala Pro Ser Ser Trp Phe Ile Asp Cys Val Met
            755                 760                 765

Ser Phe Glu Leu Leu Pro Leu Asp Ser
            770                 775

<210> 2
<211> 22
<212> DNA
<213> artificial

<220>
<223> primer

<400> 2
caccaatgcc ttatgctgga gc                                      22

<210> 3
<211> 22
<212> DNA
<213> artificial

<220>
<223> primer

<400> 3
gaagtagtga ctcctgagaa gg                                      22

<210> 4
```

```
<211>  24
<212>  DNA
<213>  artificial

<220>
<223>  primer

<400>  4
tcagctgtca agaggaagca actc                                    24

<210>  5
<211>  765
<212>  PRT
<213>  Mus musculus

<400>  5
```

| | | | | | | | | | | | | | | |
|---|---|---|---|---|---|---|---|---|---|---|---|---|---|---|

Met Pro Arg Arg Pro Pro Arg Val Cys Ser Gly Asn Gln Pro Ala Pro
1               5                   10                  15

Val Pro Ala Met Glu Pro Ala Thr Asp Gly Leu Trp Ala His Ser Arg
            20                  25                  30

Ala Ala Leu Ala Arg Leu Glu Lys Leu Leu Arg Cys Ser Arg Cys Ala
        35                  40                  45

Asn Ile Leu Lys Glu Pro Val Cys Leu Gly Gly Cys Glu His Ile Phe
    50                  55                  60

Cys Ser Gly Cys Ile Ser Asp Cys Val Gly Ser Gly Cys Pro Val Cys
65                  70                  75                  80

Tyr Thr Pro Ala Trp Ile Leu Asp Leu Lys Ile Asn Arg Gln Leu Asp
                85                  90                  95

Ser Met Ile Gln Leu Ser Ser Lys Leu Gln Asn Leu Leu His Asp Asn
            100                 105                 110

Lys Asp Ser Lys Asp Asn Thr Ser Arg Ala Ser Leu Phe Gly Asp Ala
        115                 120                 125

Glu Arg Lys Lys Asn Ser Ile Lys Met Trp Phe Ser Pro Arg Ser Lys
    130                 135                 140

Lys Val Arg Tyr Val Val Thr Lys Val Ser Val Gln Thr Gln Pro Gln
145                 150                 155                 160

Lys Ala Lys Asp Asp Lys Ala Gln Glu Ala Ser Met Tyr Glu Phe Val
                165                 170                 175

Ser Ala Thr Pro Pro Val Ala Val Pro Lys Ser Ala Lys Thr Ala Ser

```
              180                 185                 190

Arg Thr Ser Ala Lys Lys His Pro Lys Lys Ser Val Ala Lys Ile Asn
        195             200             205

Arg Glu Glu Asn Leu Arg Pro Glu Thr Lys Asp Ser Arg Phe Asp Ser
    210             215             220

Lys Glu Glu Leu Lys Glu Glu Lys Val Val Ser Cys Ser Gln Ile Pro
225             230             235             240

Val Met Glu Arg Pro Arg Val Asn Gly Glu Ile Asp Leu Leu Ala Ser
            245             250             255

Gly Ser Val Val Glu Pro Glu Cys Ser Gly Ser Leu Thr Glu Val Ser
            260             265             270

Leu Pro Leu Ala Glu His Ile Val Ser Pro Asp Thr Val Ser Lys Asn
        275             280             285

Glu Glu Thr Pro Glu Lys Lys Val Cys Val Lys Asp Leu Arg Ser Gly
    290             295             300

Gly Ser Asn Gly Asn Arg Lys Gly Cys His Arg Pro Thr Thr Ser Thr
305             310             315             320

Ser Asp Ser Cys Gly Ser Asn Ile Pro Ser Thr Ser Arg Gly Ile Gly
            325             330             335

Glu Pro Ala Leu Leu Ala Glu Asn Val Leu Val Asp Cys Ser Ser
            340             345             350

Leu Pro Ser Gly Gln Leu Gln Val Asp Val Thr Leu Arg Arg Lys Ser
        355             360             365

Asn Ala Ser Asp Asp Pro Leu Ser Leu Ser Pro Gly Thr Pro Pro Pro
    370             375             380

Leu Leu Asn Asn Ser Thr His Arg Gln Met Met Ser Ser Pro Ser Thr
385             390             395             400

Val Lys Leu Ser Ser Gly Met Pro Ala Arg Lys Arg Asn His Arg Gly
            405             410             415

Glu Thr Leu Leu His Ile Ala Ser Ile Lys Gly Asp Ile Pro Ser Val
            420             425             430
```

```
Glu Tyr Leu Leu Gln Asn Gly Asn Asp Pro Asn Val Lys Asp His Ala
        435             440             445

Gly Trp Thr Pro Leu His Glu Ala Cys Ser His Gly His Leu Lys Val
    450             455             460

Val Glu Leu Leu Leu Gln His Asn Ala Leu Val Asn Thr Pro Gly Tyr
465             470             475             480

Gln Asn Asp Ser Pro Leu His Asp Ala Val Lys Ser Gly His Ile Asp
            485             490             495

Ile Val Lys Val Leu Leu Ser His Gly Ala Ser Arg Asn Ala Val Asn
        500             505             510

Ile Phe Gly Val Arg Pro Val Asp Tyr Thr Asp Asn Glu Asn Ile Arg
        515             520             525

Ser Leu Leu Leu Pro Glu Glu Asn Glu Ser Phe Ser Thr Ser Gln
    530             535             540

Cys Ser Ile Val Asn Thr Gly Gln Arg Lys Asn Gly Pro Leu Val Phe
545             550             555             560

Ile Gly Ser Gly Leu Ser Ser Gln Gln Gln Lys Met Leu Ser Lys Leu
            565             570             575

Glu Thr Val Leu Lys Ala Lys Lys Cys Met Glu Phe Asp Ser Thr Val
            580             585             590

Thr His Val Ile Val Pro Asp Glu Glu Ala Gln Ser Thr Leu Lys Cys
        595             600             605

Met Leu Gly Ile Leu Ser Gly Cys Trp Ile Leu Lys Phe Asp Trp Val
    610             615             620

Lys Ala Cys Leu Asp Ser Lys Val Arg Glu Gln Glu Lys Tyr Glu
625             630             635             640

Val Pro Gly Gly Pro Gln Arg Ser Arg Leu Asn Arg Glu Gln Leu Leu
            645             650             655

Pro Lys Leu Phe Asp Gly Cys Tyr Phe Phe Leu Gly Gly Asn Phe Lys
            660             665             670

His His Pro Arg Asp Asp Leu Leu Lys Leu Ile Ala Ala Ala Gly Gly
        675             680             685
```

```
Lys Val Leu Ser Arg Lys Pro Lys Pro Asp Ser Asp Val Thr Gln Thr
    690             695             700
```

```
Ile Asn Thr Val Ala Tyr His Ala Lys Pro Glu Ser Asp Gln Arg Phe
705             710             715             720
```

```
Cys Thr Gln Tyr Ile Val Tyr Glu Asp Leu Phe Asn Cys His Pro Glu
                725             730             735
```

```
Arg Val Arg Gln Gly Lys Val Trp Met Ala Pro Ser Thr Trp Leu Ile
            740             745             750
```

```
Ser Cys Ile Met Ala Phe Glu Leu Leu Pro Leu Asp Ser
        755             760             765
```

<210> 6
<211> 768
<212> PRT
<213> Rattus norvegicus

<400> 6

```
Met Pro Arg Arg Pro Pro Arg Val Cys Ser Gly Asn Lys Pro Pro Pro
1               5               10              15
```

```
Val Pro Ala Met Glu Pro Ala Thr Asp Gly Leu Trp Ala His Ser Arg
                20              25              30
```

```
Ala Ala Leu Ala Arg Leu Glu Lys Leu Leu Arg Cys Ser Arg Cys Ala
            35              40              45
```

```
Asn Ile Leu Arg Glu Pro Val Cys Leu Gly Gly Cys Glu His Ile Phe
    50              55              60
```

```
Cys Ser Gly Cys Ile Ser Asp Cys Val Gly Ser Gly Cys Pro Val Cys
65              70              75              80
```

```
His Thr Pro Ala Trp Ile Leu Asp Leu Lys Ile Asn Arg Gln Leu Asp
                85              90              95
```

```
Ser Met Ile Gln Leu Tyr Ser Lys Leu Gln Asn Leu Leu His Asp Asn
                100             105             110
```

```
Lys Gly Ser Asp Ser Lys Asp Asp Thr Ser Arg Ala Ser Leu Phe Gly
            115             120             125
```

```
Asp Ala Glu Arg Lys Lys Asn Ser Val Lys Met Trp Phe Ser Pro Arg
    130             135             140
```

```
Ser Lys Lys Ile Arg Cys Val Val Asn Lys Val Ser Val Gln Thr Gln
145                 150                 155                 160

Pro Gln Lys Ala Lys Asp Asp Lys Ala Gln Glu Ala Ser Val Phe Glu
                165                 170                 175

Phe Val Ser Ala Thr Pro Pro Val Val Ser Thr Arg Ala Lys Thr
            180                 185                 190

Ala Ser Arg Thr Ser Ala Lys Lys His Pro Lys Lys Ser Val Ala Lys
            195                 200                 205

Ile Asn Arg Glu Gly Asn Phe Arg Pro Glu Thr Arg Asp Ser Arg Phe
    210                 215                 220

Asp Ser Lys Glu Lys Leu Lys Glu Glu Lys Val Val Ser Phe Ser Gln
225             230                 235                 240

Thr Leu Val Met Glu Asn Ser Arg Val Asn Gly Glu Ile Asp Leu Leu
                245                 250                 255

Ala Ser Gly Ser Val Val Glu Ser Val Phe Ser Gly Ser Phe Ala Glu
            260                 265                 270

Val Ser Leu Pro Leu Ala Glu His Ile Val Ser Pro Asp Thr Val Ser
        275                 280                 285

Lys Ser Glu Glu Ala Pro Glu Lys Lys Val Cys Val Glu Asp Arg Cys
    290                 295                 300

Pro Val Gly Ser Asp Gly Asn Pro Lys Gly Cys His Arg Pro Pro Thr
305             310                 315                 320

Ser Thr Ser Lys Lys Cys Gly Ser Asn Val Pro Ser Ala Ser Gly Glu
                325                 330                 335

Ile Arg Glu Pro Thr Leu Leu Ala Glu Asn Val Val Leu Val Asp Cys
            340                 345                 350

Ser Ser Leu Pro Ser Gly Arg Leu Gln Val Asp Val Thr Leu Arg Arg
        355                 360                 365

Gln Ser Asn Ala Ser Asp Asp Ser Leu Ser Leu Ser Pro Gly Thr Pro
    370                 375                 380

Pro Ser Leu Leu Asn Asn Ser Thr His Arg Gln Met Met Ser Lys Pro
385             390                 395                 400
```

Ser Thr Val Lys Leu Ser Ser Gly Ile Pro Ala Arg Lys Arg Asn His
            405               410              415

Arg Gly Glu Thr Leu Leu His Ile Ala Ser Ile Lys Gly Asp Ile Ser
            420             425             430

Ser Val Glu Tyr Leu Leu Gln Asn Gly Asn Asp Pro Asn Val Lys Asp
            435             440             445

His Ala Gly Trp Thr Pro Leu His Glu Ala Cys Ser His Gly His Leu
450             455             460

Lys Ile Val Glu Leu Leu Leu Gln His Asn Ala Leu Val Asn Thr Thr
465             470             475             480

Gly Tyr His Asn Asp Ser Pro Leu His Asp Ala Ala Lys Asn Gly His
            485             490             495

Ile Asp Ile Val Lys Val Leu Leu Ser His Gly Ala Ser Arg Asn Ala
            500             505             510

Val Asn Ile Phe Gly Glu Arg Pro Val Asp Tyr Thr Asp Ala Glu Asn
            515             520             525

Ile Arg Ser Leu Leu Leu Leu Pro Glu Lys Thr Asp Ser Phe Ser Thr
    530             535             540

Ser Gln Cys Ser Val Gln Val Asn Thr Gly Gln Arg Lys Ser Gly Pro
545             550             555             560

Leu Val Leu Ile Gly Ser Gly Leu Ser Ser Gln Gln Gln Lys Leu Leu
            565             570             575

Ser Lys Leu Glu Thr Val Leu Lys Ala Lys Lys Cys Ala Glu Phe Asp
            580             585             590

Asn Thr Val Thr His Val Ile Val Pro Asp Glu Glu Ala Gln Ser Thr
            595             600             605

Leu Lys Cys Met Leu Gly Ile Leu Asn Gly Cys Trp Val Leu Lys Phe
    610             615             620

Asp Trp Val Lys Ala Cys Leu Asp Ser Gln Glu Arg Glu Gln Glu Glu
625             630             635             640

Lys Tyr Glu Val Pro Gly Gly Pro Gln Arg Ser Arg Leu Asn Arg Glu

```
                    645                      650                      655

Gln Leu Leu Pro Lys Leu Phe Asp Gly Cys Tyr Phe Phe Leu Gly Gly
                     660                 665                 670

Asn Phe Lys His His Pro Lys Glu Asp Leu Leu Lys Leu Ile Ala Ala
                     675                 680                 685

Ala Gly Gly Arg Ile Leu Ser Arg Lys Pro Lys Pro Asp Ser Asp Val
                     690                 695                 700

Thr Gln Thr Ile Asn Thr Val Ala Tyr His Ala Lys Pro Asp Ser Asp
     705                 710                 715                 720

Gln Arg Phe Cys Thr Gln Tyr Ile Val Tyr Glu Asp Leu Phe Asn Cys
                     725                 730                 735

His Pro Glu Arg Val Arg Gln Gly Lys Val Trp Met Ala Pro Ser Thr
                     740                 745                 750

Trp Leu Ile Ser Cys Val Met Ala Phe Glu Leu Leu Pro Leu Asp Ser
                     755                 760                 765

<210>  7
<211>  2530
<212>  DNA
<213>  Homo sapiens

<400>  7
cagcttccct gtggtttccc gaggcttcct tgcttccgc tctgcgagga gcctttcatc      60
cgaaggcggg atgatgccgg ataatcggca gccgaggaac cggcagccga ggatccgctc    120
cgggaacgag cctcgttccg cgcccgccat ggaaccggat ggtcgcggtg cctgggccca    180
cagtcgcgcc gcgctcgacc gcctggagaa gctgctgcgc tgctcgcgtt gtactaacat    240
tctgagagag cctgtgtgtt taggaggatg tgagcacatc ttctgtagta attgtgtaag    300
tgactgcatt ggaactggat gtccagtgtg ttacaccccg gcctggatac aagacttgaa    360
gataaataga caactggaca gcatgattca actttgtagt aagcttcgaa atttgctaca    420
tgacaatgag ctgtcagatt tgaaagaaga taaacctagg aaaagtttgt taatgatgc     480
aggaaacaag aagaattcaa ttaaaatgtg gtttagccct cgaagtaaga agtcagata     540
tgttgtgagt aaagcttcag tgcaaaccca gcctgcaata aaaaagatg caagtgctca     600
gcaagactca tatgaatttg tttccccaag tcctcctgca gatgtttctg agagggctaa    660
aaaggcttct gcaagatctg gaaaaaagca aaaaagaaa actttagctg aaatcaacca    720
aaatggaat ttagaggcag aaaaagaaga tggtgaattt gactccaaag aggaatctaa    780
```

```
gcaaaagctg gtatccttct gtagccaacc atctgttatc tccagtcctc agataaatgg    840
tgaaatagac ttactagcaa gtggctcctt gacagaatct gaatgttttg gaagtttaac    900
tgaagtctct ttaccattgg ctgagcaaat agagtctcca gacactaaga gcaggaatga    960
agtagtgact cctgagaagg tctgcaaaaa ttatcttaca tctaagaaat ctttgccatt   1020
agaaaataat ggaaaacgtg gccatcacaa tagactttcc agtcccattt ctaagagatg   1080
tagaaccagc attctgagca ccagtggaga ttttgttaag caaaccgtgc cctcagaaaa   1140
tataccattg cctgaatgtt cttcaccacc ttcatgcaaa cgtaaagttg gtggtacatc   1200
agggaggaaa aacagtaaca tgtccgatga attcattagt ctttcaccag gtacaccacc   1260
ttctacatta agtagttcaa gttacaggca agtgatgtct agtccctcag caatgaagct   1320
gttgcccaat atggctgtga aagaaatca tagaggagag actttgctcc atattgcttc   1380
tattaagggc gacatacctt ctgttgaata ccttttacaa aatggaagtg atccaaatgt   1440
taaagaccat gctggatgga caccattgca tgaagcttgc aatcatgggc acctgaaggt   1500
agtggaatta ttgctccagc ataaggcatt ggtgaacacc accgggtatc aaaatgactc   1560
accacttcac gatgcagcca agaatgggca cgtggatata gtcaagctgt tactttccta   1620
tggagcctcc agaaatgctg ttaatatatt tggtctgcgg cctgtcgatt atacagatga   1680
tgaaagtatg aaatcgctat tgctgctacc agagaagaat gaatcatcct cagctagcca   1740
ctgctcagta atgaacactg ggcagcgtag ggatggacct cttgtactta taggcagtgg   1800
gctgtcttca gaacaacaga aaatgctcag tgagcttgca gtaattctta aggctaaaaa   1860
atatactgag tttgacagta cagtaactca tgttgttgtt cctggtgatg cagttcaaag   1920
taccttgaag tgtatgcttg ggattctcaa tggatgctgg attctaaaat tgaatgggt   1980
aaaagcatgt ctacgaagaa aagtatgtga acaggaagaa aagtatgaaa ttcctgaagg   2040
tccacgcaga agcaggctca acagagaaca gctgttgcca aagctgtttg atggatgcta   2100
cttctatttg tggggaacct tcaaacacca tccaaaggac aaccttatta agctcgtcac   2160
tgcaggtggg ggccagatcc tcagtagaaa gcccaagcca gacagtgacg tgactcagac   2220
catcaataca gtcgcatacc atgcgagacc cgattctgat cagcgcttct gcacacagta   2280
tatcatctat gaagatttgt gtaattatca cccagagagg gttcggcagg gcaaagtctg   2340
gaaggctcct tcgagctggt ttatagactg tgtgatgtcc tttgagttgc ttcctcttga   2400
cagctgaata ttataccaga tgaacatttc aaattgaatt tgcacggttt gtgagagccc   2460
agtcattgta ctgttttta tgttcacatt tttacaaata ggtagagtca ttcatatttg   2520
tctttgaatc                                                          2530
```

<210> 8
<211> 2568

<212> DNA
<213> Mus musculus

<400> 8

| | | | | | |
|---|---|---|---|---|---|
| ctccgagccg | gaggcgtccg | accaattcag | agactccgca | cgcagcagga | tccggcggtg | 60
| accagcgggg | tgcggcgcta | gagcaaacct | gacctcccct | cctctgtggg | aatgccacgc | 120
| cggccgccga | gggtctgctc | tgggaaccag | cctgctcccg | tgcccgccat | ggagccggct | 180
| accgacgggc | tttgggccca | cagccgcgcg | gcgcttgccc | gcctggagaa | gctgctgcgc | 240
| tgctcccgct | gtgctaatat | tctgaaggag | cccgtgtgct | taggaggatg | tgagcacatc | 300
| ttctgtagtg | gttgtataag | tgactgtgtt | ggctcaggat | gcccagtgtg | ttacacccca | 360
| gcctggatcc | tagacctcaa | gataaaccga | caattggaca | gcatgatcca | gctttctagt | 420
| aagctccaaa | atttgctcca | tgacaataaa | gattcaaaag | acaacacatc | tagggcaagt | 480
| ttatttggtg | atgcagaaag | gaagaagaat | tcaataaaaa | tgtggtttag | tcctcgaagt | 540
| aagaaggtta | gatatgttgt | gactaaagtg | tcagtacaaa | cacagcctca | aaaggcaaag | 600
| gacgacaaag | cccaggaagc | ctcaatgtat | gaatttgttt | ccgcaactcc | ccctgtagct | 660
| gttcctaaga | gtgctaaaac | agcttctaga | acatctgcaa | aaaagcatcc | aaagaaatct | 720
| gtagctaaga | tcaacaggga | ggagaattta | aggccagaaa | caaggatag | tagatttgat | 780
| tccaaagagg | agctgaagga | agagaaggtt | gtctcctgta | gccaaatacc | agttatggag | 840
| agaccacggg | taaatggtga | aatagactta | ttagcaagtg | gttctgttgt | agaacctgaa | 900
| tgttctggaa | gcttgactga | agtctcttta | ccattggctg | agcatatagt | gtctccagac | 960
| actgtgagca | agaatgaaga | gactccggag | aagaaggtct | gtgtaaaaga | tcttcgttca | 1020
| ggagggagta | atggaaatcg | taaaggctgc | cacaggccta | ccacttctac | ttctgacagt | 1080
| tgtgggagca | acattccgag | caccagcaga | ggcatcggtg | agccagcatt | gcttgcagaa | 1140
| aacgtagtgt | tggttgactg | ctcttcactg | ccttcaggcc | agctacaggt | tgatgtcaca | 1200
| ctcaggagaa | agagtaacgc | atcagatgac | ccccttagcc | tttcaccggg | cacaccccca | 1260
| cctytgctga | acaattcaac | tcacagacaa | atgatgtcaa | gcccctccac | agtgaagctg | 1320
| tcttctggta | tgccagccag | gaaagaaat | cacagaggag | agaccttact | tcatattgct | 1380
| tctattaagg | gtgatatacc | ttctgttgaa | tacctcttgc | aaaatggaaa | cgacccaaat | 1440
| gttaaagacc | atgctggatg | gacaccgttg | catgaagcct | gcagtcatgg | gcacctgaag | 1500
| gtagtggagt | tgctgctcca | gcataatgcc | ctggtgaaca | cccctggcta | tcagaatgac | 1560
| tcgccactcc | acgatgccgt | caagagtggc | cacatcgata | tagtcaaggt | gttactgtcc | 1620
| cacggtgctt | ccaggaatgc | tgttaacata | tttggtgtgc | ggcctgtgga | ctatacagac | 1680
| aatgagaata | taagatcatt | attgctgctg | ccagaggaga | atgaatcatt | ctcaactagc | 1740
| cagtgctcta | tcgtgaacac | cgggcagcga | aagaatgggc | cgctggtatt | tataggcagt | 1800

```
gggcttcctt cacagcagca gaaaatgctc agcaaacttg agacagttct taaggctaaa    1860
aagtgtatgg aatttgacag tacagtaact catgtcattg ttcctgatga ggaagcgcag    1920
agtactctga agtgtatgct tgggattctc agtggatgct ggatcctgaa gtttgattgg    1980
gtgaaagcct gtctggacag caaagtacgt gagcaggaag aaaagtatga agttcctgga    2040
ggtccacaga ggagcaggct caacagagag cagctgttgc caaagctgtt tgatggatgc    2100
tacttctttt tggggggaaa cttcaagcat catccaaggg atgacctcct taagctcatt    2160
gctgcagcag gaggcaaagt cctgagtcgc aagcccaagc cagacagtga tgtgactcag    2220
accatcaaca cggttgcata ccatgccaag cctgagtcgg atcagcgctt ctgtacgcag    2280
tacatcgtct acgaagacct gtttaactgt cacccagaga gggttcggca gggcaaagtc    2340
tggatggctc cgtccacctg gcttatcagc tgtataatgg cctttgaatt gcttcctctt    2400
gacagctgaa tgtcatacca ggtgaacatt ttaagttgga catgcatggt ttgtaagaac    2460
aacggccatt gtgatatttc tggtcattca tgtttttatg aataggtaga accattcata    2520
tttcttcccc ctttgaattg caaataaaa caattgatag taaaaaaa              2568
```

<210> 9
<211> 152
<212> PRT
<213> Rattus norvegicus

<400> 9

Ser His Gly His Leu Lys Ile Val Glu Leu Leu Gln His Asn Ala
1               5                   10                  15

Leu Val Asn Thr Thr Gly Tyr His Asn Asp Ser Pro Leu His Asp Ala
            20                  25                  30

Ala Lys Asn Gly His Ile Asp Ile Val Lys Val Leu Leu Ser His Gly
        35                  40                  45

Ala Ser Arg Asn Ala Val Asn Ile Phe Gly Glu Arg Pro Val Asp Tyr
    50                  55                  60

Thr Asp Ala Glu Asn Ile Arg Ser Leu Leu Leu Pro Glu Lys Thr
65                  70                  75                  80

Asp Ser Phe Ser Thr Ser Gln Cys Ser Val Gln Val Asn Thr Gly Gln
                85                  90                  95

Arg Lys Ser Gly Pro Leu Val Leu Ile Gly Ser Gly Leu Ser Ser Gln
                100                 105                 110

```
Gln Gln Lys Leu Leu Ser Lys Leu Glu Thr Val Leu Lys Ala Lys Lys
        115             120             125

Cys Ala Glu Phe Asp Asn Thr Val Thr His Val Ile Val Pro Asp Glu
        130             135             140

Glu Ala Gln Ser Thr Leu Lys Cys
145             150
```

<210> 10
<211> 2499
<212> DNA
<213> Rattus norvegicus

<400> 10

| | | | | | |
|---|---|---|---|---|---:|
| gaattcacta | gtgattatgc | cacgccggcc | gccgagggtc | tgctccggga | acaagcctcc | 60 |
| tcccgtgccc | gccatggaac | cagctaccga | cgggctttgg | gcccacagcc | gtgcggcgct | 120 |
| tgcccgtctg | gagaagttgt | tgcgctgctc | ccgctgtgct | aatattctga | gggagcccgt | 180 |
| gtgcctagga | ggatgcgagc | acatcttctg | tagtggttgt | ataagcgact | gtgttggatc | 240 |
| aggatgccca | gtgtgtcata | ccccagcctg | gatcctagac | ctcaagataa | acagacagtt | 300 |
| ggacagcatg | atccagcttt | atagtaagct | tcaaaatttg | ctacatgaca | ataaaggttc | 360 |
| agattcaaaa | gacgacacat | ctagggcaag | tttatttggt | gatgcagaaa | ggaagaagaa | 420 |
| ttcagtaaaa | atgtggttta | gtcctcgaag | taagaaaatt | agatgtgttg | tgaataaagt | 480 |
| ttcagtacaa | acccagcctc | aaaaggcaaa | ggatgacaaa | gcccaggaag | cctcagtgtt | 540 |
| tgaatttgtt | tccgcaactc | cccctgtagt | tgtttctacg | agggctaaaa | cagcttcaag | 600 |
| aacatctgca | aaaaagcatc | ccaagaaatc | tgtagctaag | atcaaccggg | agggaaattt | 660 |
| caggccagaa | acaagggata | gtagatttga | ttccaaagaa | aagctgaagg | aagagaaggt | 720 |
| tgtctccttt | agccaaacac | tagttatgga | gaattcacgg | gtaaatggcg | aaatagactt | 780 |
| attagcgagt | ggctctgtgg | tagaatccgt | cttctctggc | agctttgctg | aagtctcttt | 840 |
| accattggct | gagcatatag | tgtctccaga | tactgtgagc | aagagtgaag | aggctcctga | 900 |
| gaagaaggtc | tgtgtagaag | atcgttgtcc | agtagggagt | gatggaaatc | ccaaaggctg | 960 |
| ccacaggcct | cccacttcta | cttctaagaa | atgcgggagc | aacgttccaa | gcgccagcgg | 1020 |
| agaaatccgt | gagccaacat | tgcttgcaga | aaatgtagtg | ttggttgact | gttcttcact | 1080 |
| gccttcaggc | cgacttcagg | ttgatgtcac | cctcaggaga | cagagtaacg | catcagatga | 1140 |
| ctctcttagc | ctttcaccag | gcacaccccc | atctctgctg | aacaattcca | ctcacagaca | 1200 |
| aatgatgtca | agccctcca | cagtgaagct | gtcttctggt | attccagcca | ggaaaagaaa | 1260 |
| tcacagagga | gagacgttac | tgcacattgc | ctctataaag | ggtgatatat | cttctgttga | 1320 |
| atacctcttg | caaatggaa | acgacccaaa | tgttaaggac | catgctggat | ggacaccgtt | 1380 |

```
gcatgaagcc tgcagtcatg ggcacctgaa gatagtggag ctgctgctcc agcacaatgc    1440
cttggtgaac accaccggct atcacaatga ctcgccactg cacgatgccg ccaagaatgg    1500
ccacatcgat atagtcaagg tgttactgtc ccacggagct tccaggaacg ctgttaacat    1560
atttggtgag cggccagtgg attacacaga cgctgagaat ataaggtcat tattgctgct    1620
gccagagaag acggattcat tctcaactag ccagtgctct gtccaggtga acaccgggca    1680
gcggaagagt gggccgctgg tactaatagg cagtgggctt tcttcacagc agcagaaact    1740
gctcagcaaa cttgagacag tgctaaaggc taagaagtgt gctgagtttg acaacacagt    1800
aactcatgtc attgttcctg atgaggaagc tcagagtacc ttgaagtgta tgcttgggat    1860
tctcaatgga tgctgggtcc tgaagtttga ttgggtgaaa gcctgtttgg acagccaaga    1920
acgtgagcag gaagaaaagt atgaagttcc tggaggtccg cagaggagca ggctcaacag    1980
agagcagctg ctgcccaaac tgttcgatgg atgctacttc tttctggggg ggaacttcaa    2040
acatcatcca aaagaagacc tcctgaagct cattgctgca gcaggaggca gaatcctcag    2100
cagaaagccc aagccagaca gtgacgtgac tcagaccatc aacacggttg cataccatgc    2160
caagcctgac tctgatcagc gcttctgtac gcagtacatt gtctatgagg atctgttaa    2220
ctgtcaccca gagagggttc ggcagggcaa agtctggatg gctccttcca cctggctaat    2280
cagctgtgta atggcctttg agttgcttcc tcttgacagc tgaatgtcgt accaggtgaa    2340
cattttaagt tgaaggcgcg tggtttgtga gaacacggcc attgtgatgt ttgatcactc    2400
tcgcttttat ggataggtag aaccattcat atccccctc cctttgaatt gcaaaataaa    2460
acaattgata aaggaaaaaa aaaaaaaaaa aaaaaaaa                             2499
```

```
<210> 11
<211> 6
<212> PRT
<213> artificial sequence

<220>
<223> synthetic peptide

<220>
<221> MOD_RES
<222> (1)..(1)
<223> Xaa is Benzyloxycarbonyl

<220>
<221> MOD_RES
<222> (6)..(6)
<223> Xaa is fluoromethylketone

<400> 11

Xaa Asp Glu Val Asp Xaa
1               5
```

```
<210>   12
<211>   6
<212>   PRT
<213>   artificial sequence

<220>
<223>   synthetic peptide

<220>
<221>   MOD_RES
<222>   (1)..(1)
<223>   Xaa is Benzyloxycarbonyl

<220>
<221>   MOD_RES
<222>   (6)..(6)
<223>   Xaa is fluoromethylketone

<400>   12

Xaa Val Glu Ile Asp Xaa
1               5
```